US011266607B2

(12) United States Patent
Shlieout et al.

(10) Patent No.: US 11,266,607 B2
(45) Date of Patent: *Mar. 8, 2022

(54) PROCESS FOR THE MANUFACTURE AND USE OF PANCREATIN MICROPELLET CORES

(75) Inventors: George Shlieout, Sehnde (DE); Claus-Juergen Koelln, Neustadt (DE); Frithjof Sczesny, Hannover (DE); Jens Onken, Barsinghausen (DE); Guido Ruesing, Neustadt (DE)

(73) Assignee: ABBVIE PHARMACEUTICALS GMBH, Ludwigshafen am Rhein (DE)

( * ) Notice: Subject to any disclaimer, the term of this patent is extended or adjusted under 35 U.S.C. 154(b) by 934 days.

This patent is subject to a terminal disclaimer.

(21) Appl. No.: 11/464,704

(22) Filed: Aug. 15, 2006

(65) Prior Publication Data
US 2007/0148152 A1 Jun. 28, 2007

Related U.S. Application Data

(60) Provisional application No. 60/708,526, filed on Aug. 15, 2005, provisional application No. 60/708,692, filed on Aug. 15, 2005.

(51) Int. Cl.
*A61K 9/50* (2006.01)
*A61K 9/16* (2006.01)
*A61K 38/46* (2006.01)

(52) U.S. Cl.
CPC .......... *A61K 9/5042* (2013.01); *A61K 9/1635* (2013.01); *A61K 38/46* (2013.01)

(58) Field of Classification Search
CPC .............................. A61K 9/5042; A61K 38/46
See application file for complete search history.

(56) References Cited

U.S. PATENT DOCUMENTS

| | | |
|---|---|---|
| 3,324,002 A | 6/1967 | Antonides |
| 3,803,305 A | 4/1974 | Thuillier |
| 3,950,508 A | 4/1976 | Mony et al. |
| 3,956,483 A | 5/1976 | Lewis |
| 3,986,927 A | 10/1976 | Melnick et al. |
| 3,991,180 A | 11/1976 | Boettner et al. |
| 4,019,958 A | 4/1977 | Hell et al. |
| 4,079,125 A | 3/1978 | Sipos |
| 4,106,991 A | 8/1978 | Markussen et al. |
| 4,242,219 A | 12/1980 | Bogerman et al. |
| 4,280,971 A * | 7/1981 | Wischniewski .......... A61P 1/00 264/15 |
| 4,447,412 A | 5/1984 | Bilton |
| 4,490,361 A | 12/1984 | Heldebrant |
| 4,533,562 A | 8/1985 | Ikegami et al. |
| 4,623,624 A | 11/1986 | Schultze |
| 4,689,297 A | 8/1987 | Good et al. |
| 4,775,536 A | 10/1988 | Patell |
| 4,786,505 A | 11/1988 | Lovgren et al. |
| 4,929,774 A | 5/1990 | Fukamachi et al. |
| 5,068,110 A | 11/1991 | Fawzi et al. |
| 5,219,572 A | 6/1993 | Sivaramakrishnan et al. |
| 5,225,202 A * | 7/1993 | Hodges ................ A61K 9/5073 424/461 |
| 5,260,074 A * | 11/1993 | Sipos ........................... 424/497 |
| 5,300,433 A | 4/1994 | Hrinda et al. |
| 5,302,400 A | 4/1994 | Sipos |
| 5,324,649 A | 6/1994 | Arnold et al. |
| 5,374,657 A | 12/1994 | Kyle |
| 5,378,462 A * | 1/1995 | Boedecker .......... A61K 9/1641 424/94.21 |
| 5,489,530 A | 2/1996 | Braatz et al. |
| 5,536,661 A | 7/1996 | Boel et al. |
| 5,558,071 A * | 9/1996 | Ward ........................ F02P 3/02 123/598 |
| 5,570,104 A | 10/1996 | Hayashi |
| 5,614,189 A | 3/1997 | Huge-Jensen |
| 5,618,710 A | 4/1997 | Navia et al. |
| 5,645,832 A | 7/1997 | Braatz et al. |
| 5,658,871 A | 8/1997 | Batenburg et al. |
| 5,719,115 A | 2/1998 | Paatz et al. |
| 5,725,880 A | 3/1998 | Hirakawa et al. |
| 5,750,104 A | 5/1998 | Sipos |
| 5,750,148 A | 5/1998 | Maruyama et al. |
| 5,766,912 A | 6/1998 | Boel et al. |
| 5,783,545 A | 7/1998 | Paatz et al. |
| 5,801,022 A | 9/1998 | Navia et al. |
| 5,849,296 A | 12/1998 | Navia et al. |

(Continued)

FOREIGN PATENT DOCUMENTS

| | | |
|---|---|---|
| CA | 2263703 | 8/1999 |
| DE | 2035739 A1 | 1/1972 |

(Continued)

OTHER PUBLICATIONS

21 CFR 201.302 "Notice to manufacturers, packers, and distributors of drugs for internal use which contain mineral oil" (Apr. 2001).*
Marumerizer® QJ-1000T Spheronizer. (http://www.lcicorp.com/industrial_granulation/detail/category/marumerizer_qj1000); accessed Jul. 26, 2013.*
21 CFR 201.302; published Apr. 1, 1996 (http://www.gpo.gov/fdsys/pkg/CFR-1996-title21-vol4/pdf/CFR-1996-title21-vol4-sec201-302.pdf).*
Rudnic, E.M.; Schwartz, J.B. "Oral Solid Dosage Forms" Remington: The Science and Practice of Pharmacy, 21st Edition. 2005. Chapter 45. pp. 889-928.*
Buhler, V. "Polyvinylpyrrolidone Excipients for Pharmaceuticals" 2005, pp. 1-254.*
Luwa (http://www.lcicorp.com/industrial_granulation) accessed Dec. 16, 2015.*
Rudnic, E.M.; Schwartz, J.B. "Oral Solid Dosage Forms" Remington: The Science and Practice of Pharmacy, 21st Edition. 2005. Chapter 45. pp. 889-928. (Year: 2005).*

(Continued)

*Primary Examiner* — Andrew S Rosenthal

(57) ABSTRACT

A process for manufacturing and using pancreatin micropellet cores and pancreatin micropellets which are substantially free of synthetic oils. In one embodiment, a pharmaceutical composition is provided comprising a pancreatin micropellet with the enteric coating being designed to deliver pancreatin to the upper portion of the intestine of a mammal for release.

101 Claims, No Drawings

(56) References Cited

U.S. PATENT DOCUMENTS

| | | | |
|---|---|---|---|
| 5,855,914 A * | 1/1999 | Koyama | A61K 9/1676 424/461 |
| 5,863,759 A | 1/1999 | Boel et al. | |
| 5,869,438 A | 2/1999 | Svendsen et al. | |
| 5,874,558 A | 2/1999 | Boel et al. | |
| 5,879,920 A | 3/1999 | Dale et al. | |
| 5,976,529 A | 11/1999 | Navia et al. | |
| 5,993,806 A | 11/1999 | Galle | |
| 6,004,768 A | 12/1999 | Navia et al. | |
| 6,011,001 A | 1/2000 | Navia et al. | |
| 6,025,391 A | 2/2000 | Haeberlin et al. | |
| 6,030,798 A | 2/2000 | Braatz et al. | |
| 6,051,220 A | 4/2000 | Scharpe | |
| 6,054,136 A | 4/2000 | Farah et al. | |
| 6,140,475 A | 10/2000 | Margolin et al. | |
| 6,187,572 B1 | 2/2001 | Platz et al. | |
| 6,224,910 B1 | 5/2001 | Ullah et al. | |
| 6,267,985 B1 | 7/2001 | Chen et al. | |
| 6,278,794 B1 | 8/2001 | Parekh et al. | |
| 6,312,704 B1 | 11/2001 | Farah et al. | |
| 6,348,442 B2 | 2/2002 | Markussen | |
| 6,355,461 B2 | 3/2002 | Henriksen et al. | |
| 6,426,091 B1 | 7/2002 | Okumura et al. | |
| 6,579,851 B2 * | 6/2003 | Goeke | A61K 38/26 514/11.7 |
| 6,692,771 B2 | 2/2004 | Pather et al. | |
| 6,734,188 B1 | 5/2004 | Rhodes et al. | |
| 6,749,851 B2 | 6/2004 | Mann et al. | |
| 6,767,729 B1 | 7/2004 | Nagano et al. | |
| 7,122,357 B2 * | 10/2006 | Sander-Struckmeier | A61K 38/465 435/183 |
| 7,211,281 B2 | 5/2007 | Van Beek et al. | |
| 7,479,378 B2 | 1/2009 | Potthoff et al. | |
| 7,658,918 B1 | 2/2010 | Ortenzi | |
| 8,221,747 B2 | 7/2012 | Ortenzi | |
| 8,246,950 B2 | 8/2012 | Ortenzi | |
| 8,461,129 B2 * | 6/2013 | Bolduc | A61L 15/28 127/49 |
| 2001/0046493 A1 | 11/2001 | Margolin et al. | |
| 2002/0061302 A1 * | 5/2002 | Sander-Struckmeier | A61K 38/47 424/94.21 |
| 2002/0137156 A1 | 9/2002 | Margolin et al. | |
| 2002/0146451 A1 | 10/2002 | Sharma et al. | |
| 2003/0007962 A1 | 1/2003 | Vergez et al. | |
| 2003/0017144 A1 | 1/2003 | Margolin et al. | |
| 2003/0021844 A1 | 1/2003 | Barthelemy et al. | |
| 2003/0049245 A1 | 3/2003 | Mann et al. | |
| 2003/0086948 A1 | 5/2003 | Benameur et al. | |
| 2003/0104048 A1 | 6/2003 | Petal et al. | |
| 2003/0175259 A1 | 9/2003 | Karageozian et al. | |
| 2003/0180352 A1 | 10/2003 | Patel et al. | |
| 2003/0211127 A1 | 11/2003 | Margolin et al. | |
| 2004/0013697 A1 | 1/2004 | Berndl et al. | |
| 2004/0033220 A1 | 2/2004 | Hartmann | |
| 2004/0057944 A1 | 3/2004 | Galle et al. | |
| 2004/0101562 A1 * | 5/2004 | Maio | A61K 9/50 424/488 |
| 2004/0161423 A1 | 8/2004 | Kumar | |
| 2004/0202643 A1 | 10/2004 | Margolin et al. | |
| 2004/0213847 A1 | 10/2004 | Matharu et al. | |
| 2005/0163847 A1 | 7/2005 | Cheng et al. | |
| 2005/0250817 A1 | 11/2005 | Shlieout | |
| 2007/0148151 A1 | 6/2007 | Frink | |
| 2007/0148152 A1 | 6/2007 | Shlieout et al. | |
| 2007/0148153 A1 | 6/2007 | Shlieout | |
| 2007/0178120 A1 | 8/2007 | Morrison et al. | |
| 2008/0019959 A1 | 1/2008 | Becher et al. | |
| 2008/0226713 A1 * | 9/2008 | Bodenteich | A61P 25/16 424/468 |
| 2008/0292610 A1 | 11/2008 | Hartmann | |
| 2009/0130063 A1 | 5/2009 | Becher et al. | |
| 2009/0226414 A1 | 9/2009 | Tijssen et al. | |
| 2011/0028412 A1 * | 2/2011 | Cappello | A61K 31/7004 514/25 |
| 2013/0041004 A1 * | 2/2013 | Drager | A61K 9/08 514/394 |
| 2013/0084243 A1 * | 4/2013 | Goetsch | C07K 16/2863 424/1.49 |
| 2013/0096073 A1 * | 4/2013 | Sidelman | A61K 38/1709 514/21.6 |

FOREIGN PATENT DOCUMENTS

| | | |
|---|---|---|
| DE | 2410241 A1 | 9/1975 |
| DE | 2512746 A1 | 9/1976 |
| DE | 2626109 A1 | 12/1976 |
| DE | 2923279 C2 | 11/1980 |
| DE | 3642853 A1 | 6/1988 |
| DE | 4203315 A1 | 8/1992 |
| DE | 4200002 | 7/1993 |
| DE | 4322229 A1 | 1/1995 |
| DE | 4344215 A1 | 6/1995 |
| DE | 19907764 A1 | 11/1999 |
| DE | 19848849 A1 | 4/2000 |
| DE | 19856415 | 6/2000 |
| DE | 10012095 A1 | 9/2000 |
| DE | 29824797 U1 | 8/2002 |
| EP | 0008780 A2 | 3/1980 |
| EP | 0019253 A1 | 11/1980 |
| EP | 0021129 A2 | 1/1981 |
| EP | 0035780 | 9/1981 |
| EP | 0141607 A2 | 5/1985 |
| EP | 0170360 A1 | 2/1986 |
| EP | 0193829 A2 | 9/1986 |
| EP | 0206417 A2 | 12/1986 |
| EP | 0238023 | 9/1987 |
| EP | 0304331 A2 | 2/1989 |
| EP | 0304332 A2 | 2/1989 |
| EP | 0305216 | 3/1989 |
| EP | 0326026 B1 | 8/1989 |
| EP | 0458845 A1 | 8/1990 |
| EP | 0458849 A1 | 8/1990 |
| EP | 0407225 A1 | 1/1991 |
| EP | 0600868 A1 | 12/1991 |
| EP | 0550450 A1 | 2/1992 |
| EP | 0592478 A1 | 1/1993 |
| EP | 0583726 A2 | 2/1994 |
| EP | 0691982 B1 | 1/1996 |
| EP | 0828509 A1 | 12/1996 |
| EP | 0826375 B1 | 3/1998 |
| EP | 0973878 A1 | 10/1998 |
| EP | 0897985 A2 | 2/1999 |
| EP | 1010423 A2 | 6/2000 |
| EP | 1138833 B1 | 4/2001 |
| EP | 1186658 | 3/2002 |
| EP | 1261368 A2 | 12/2002 |
| EP | 1279402 A1 | 1/2003 |
| EP | 05107472 | 8/2005 |
| EP | 05107474 | 8/2005 |
| EP | 1593688 | 11/2005 |
| EP | 2278002 | 1/2011 |
| FR | 2313916 A1 | 1/1977 |
| GB | 1509866 | 5/1978 |
| JP | 04936885 A | 4/1974 |
| JP | 58148814 A | 9/1983 |
| JP | 58179492 | 10/1983 |
| JP | 59169491 A | 9/1984 |
| JP | 61162185 | 7/1986 |
| JP | 62-029950 | 2/1987 |
| JP | 04-023991 | 1/1992 |
| JP | 4187085 A | 7/1992 |
| JP | 8143457 A | 6/1996 |
| JP | 09125096 A | 5/1997 |
| WO | WO 82/03871 | 11/1982 |
| WO | 1987/07292 A1 | 12/1987 |
| WO | 1989/08694 A1 | 9/1989 |
| WO | 1989/08695 A1 | 9/1989 |
| WO | 1991/06638 A1 | 5/1991 |
| WO | 91/07948 | 6/1991 |
| WO | 91/014454 A1 | 10/1991 |

(56) References Cited

FOREIGN PATENT DOCUMENTS

| | | |
|---|---|---|
| WO | WO 91/16060 | 10/1991 |
| WO | WO 91/18623 | 12/1991 |
| WO | WO 92/02617 | 2/1992 |
| WO | 1992/12645 A1 | 8/1992 |
| WO | 1992/13030 A1 | 8/1992 |
| WO | WO 93/00924 | 1/1993 |
| WO | 1993/07260 A1 | 4/1993 |
| WO | 1993/07263 A1 | 4/1993 |
| WO | 93/18790 | 9/1993 |
| WO | WO 94/08603 | 4/1994 |
| WO | WO 95/07688 | 3/1995 |
| WO | WO 95/08983 | 4/1995 |
| WO | WO 95/15681 | 6/1995 |
| WO | 1995/22625 A1 | 8/1995 |
| WO | 96/038170 A1 | 12/1995 |
| WO | 1996/00343 A1 | 1/1996 |
| WO | 1996/16151 A1 | 5/1996 |
| WO | 1996/38527 A1 | 12/1996 |
| WO | 1997/23605 A1 | 7/1997 |
| WO | 1997/39116 A1 | 10/1997 |
| WO | WO 97/42980 | 11/1997 |
| WO | WO 98/00169 | 1/1998 |
| WO | WO 98/38292 | 9/1998 |
| WO | WO 98/46732 | 10/1998 |
| WO | WO 98/52561 | 11/1998 |
| WO | WO 99/20745 | 4/1999 |
| WO | WO 99/28344 | 6/1999 |
| WO | 99/044589 A1 | 9/1999 |
| WO | 2000/01793 A1 | 1/2000 |
| WO | WO 00/34510 | 6/2000 |
| WO | WO 00/54799 | 9/2000 |
| WO | WO 01/01960 | 1/2001 |
| WO | 2001/25412 A1 | 4/2001 |
| WO | 01/037808 A1 | 5/2001 |
| WO | 2001/58276 A2 | 8/2001 |
| WO | WO 01/68139 | 9/2001 |
| WO | 2002/20746 A1 | 3/2002 |
| WO | 2002/28369 A1 | 4/2002 |
| WO | 02/40045 | 5/2002 |
| WO | WO 02/36156 | 5/2002 |
| WO | 02/060474 A2 | 8/2002 |
| WO | WO 03/047595 | 6/2003 |
| WO | 2003/055967 A1 | 7/2003 |
| WO | 2003/080827 A2 | 10/2003 |
| WO | WO 2004/007707 | 1/2004 |
| WO | 2004/069872 A1 | 8/2004 |
| WO | WO 2005/012911 | 2/2005 |
| WO | 2005/070962 A1 | 8/2005 |
| WO | WO 2005/092370 | 10/2005 |
| WO | 2006/044529 A1 | 4/2006 |
| WO | 2006/136159 A2 | 12/2006 |
| WO | 2007/020260 A2 | 2/2007 |
| WO | 2007020259 | 2/2007 |
| WO | WO 2007/014896 | 2/2007 |
| WO | WO 2007/135125 | 11/2007 |
| WO | 2008/079685 A2 | 7/2008 |

OTHER PUBLICATIONS

Buhler, V. "Polyvinylpyrrolidone Excipients for Pharmaceuticals" 2005, pp. 1-254. (Year: 2005).*
Luwa (http://www.lcicorp.com/industrial_granulation) accessed Dec. 16, 2015. (Year: 2015).*
LCI (https://lcicorp.com/spheronizers/marumerizer_spheronizers/) accessed Jul. 30, 2018, pp. 1-4 (Year: 2018).*
ILGA.gov (http://www.ilga.gov/legislation/legisnet91/hbgroups/hb/910HB4718LV.html) 2001, pp. 1-6 (Year: 2001).*
Frank-Kamenetskaya, O.V. et al. "The Effect of the Environment on Saint Petersburg's Cultural Heritage" Springer, 2016, pp. 1-188 (Year: 2016).*
21 CFR 201.302; published Apr. 1, 1996 (http://www.gpo.gov/fdsys/pkg/CFR-1996-title21-vol4/pdf/CFR-1996-title21-vol4-sec201-302.pdf) (Year: 1996).*
IMA Zanchetta Rotolab (https://www.fdm24.com/en/datasheet/usetec/1300-01-0284_IMA+Zanchetta-Rotolab.pdf) accessed Jun. 23, 2021, p. 1 (Year: 2021).*
Directive 2003/36/EC of the European Parliament and of the Council of May 26, 2003, Official Journal of the European Union, p. L 156/26-30.
Turner et al., The Inactivation of Viruses in Pig Slurries: A Review, Bioresource Technology, vol. 61 (1997) p. 9-20.
Braeuniger et al., Further studies on thermal resistance of bovine parvovirus against moist and dry heat, Int. J. Hyg. Environ. Health, vol. 203 (2000) p. 71-75.
Committee For Proprietary Medicinal Products, Note For Guidance on Virus Validation Studies: The Design, Contribution and Interpretation of Studies Validating the Inactivation and Removal of Viruses, The European Agency for the Evaluation of Medicinal Products, Feb. 14, 1996, p. 1-13.
Thomson et al., Ch. 73 Porcine parvovirus infection, Infectious Diseases of Livestock vol. 2 (2nd ed. 2004) p. 806-814.
Guidance for Industry SUPAC-MR, Modified Release Solid Oral Dosage Forms, Sep. 1997, p. 1-36.
21 CFR 201.302 Notice to manufacturers, packers, and distributors of drugs for internal use which contain mineral oil, Apr. 2000.
International Search Report for PCT/EP2006/065313, dated Feb. 2, 2007.
Written Opinion of the International Searching Authority for PCT/EP2006/065313, dated Feb. 2, 2007.
Chemical Abstract, No. 99:200535j, "Capsules Containing Stable Digestive Enzymes", vol. 99, p. 342 (1983).
D'Costa, D., "Diabetic Neuropathic Cachexia Associated with Malabsorption," Diabetic Medicine, vol. 9/2, pp. 203-205 (1992).
Delhaye, M., "Comparative Evaluation of a High Lipase Pancreatic Enzyme Preparation and a Standard Pancreatic Supplement for Treating Exocrine Pancreatic Insufficiency in Chronic Pancreatitis," European Journal of Gastronenterology and Hepatology, vol. 8/7, pp. 699-703 (1996).
European Search Report for European Patent Application No. EP93112848 (dated Apr. 15, 1994).
European Search Report for European Patent Application No. EP 05733481.5 (dated Oct. 1, 2007).
Fiedler, Herbert P. (Lexikon der Hilfsstoffe fuer Pharmazie, Kosmetik und Angrenzende Gebiete, 5 Aufli. 2002), Encyclopedia of Excipients for Pharmaceuticals, Cosmetics and Related Areas, vol. 5, pp. 733 and 995, including English translation (cover page, pp. 747 & 921) (Total: Six (6) pages). Printed and bound by R. Oldenbourg Graphische Betriebe Druckerel GmbH, Kirchheim, Germany.
ICH Harmonised Tripartite Guideline, Table of Content and pp. 1-16, (1999).
International Preliminary Report of Patentability for PCT/EP2006/064717 (dated Oct. 11, 2007).
International Preliminary Report of Patentability for PCT/EP2006/065311 (dated Feb. 20, 2008).
International Preliminary Report of Patentability for PCT/EP2006/065313 (dated Feb. 20, 2008).
International Preliminary Report of Patentability for PCT/EP2007/054880 (dated Nov. 27, 2008).
International Search Report for PCT/EP2000/002261 (dated Jul. 11, 2000).
International Search Report and Written Opinion for PCT/EP2006/064717 (dated Nov. 20, 2006).
International Search Report and Written Opinion for PCT/EP2006/065311 (dated Feb. 2, 2007).
International Search Report and Written Opinion for PCT/EP2007/054880 (dated Oct. 2, 2007).
Nakamura, et al., Pancreas, vol. 16(3), pp. 329-336, (1998).
"Pancreatin", The American Heritage Dictionary of the English Language, 4th Edition Boston, Houghton Mifflin (2002). www.bartleby.com/61/ (printed Mar. 21, 2007).
"Pancreatin juice", The American Heritage Dictionary of the English Language, 4th Edition Boston, Houghton Mifflin (2002). www.bartleby.com/61/ (printed Mar. 21, 2007).
Simek, I., "Substitution Therapy in Insufficient External Pancreatic Secretion," Online Medline Databse (1993).

(56) References Cited

OTHER PUBLICATIONS

Subramanian et al., "Effect of lipid excipients on in vitro pancreatic lipase activity," Drug Dev. Ind. Pharm., vol. 29(8), pp. 885-890 (2003).
Tischer et al., "Replication of procine circovirus: induction by glucosamine and cell cycle dependence," Archives of Virology, vol. 96, pp. 39-57 (1987).
Ullman's Encyclopedia, pp. 175-176, 179, 180, and 199, (1987).
Eurand S.A., Notice of Opposition against the European Patent No. EP 1931317., dated Sep. 23, 2009.
McGinity, Aqueous Polymeric Coatings for Pharmaceutical Dosage, Marcel Dekker, Inc., 1989.
Murthy, et al., "In Vitro Release Characteristics of Hard Shell Capsule Products Coated with Aqueous- and Organic-Based Enteric Polymers," Journal of Biomaterials Application, J. Biomater Appl., vol. 3, pp. 52-79 (1988), available at http://jba.sagepub.com.
Nordmark Arzneimittel GmbH & Co. KG, Notice of Opposition against the European Patent No. EP 1931317., Aug. 6, 2009 with translation.
Oshima, et al., "Preparation of Rapidly Disintegrating Tablets Containing Itraconazole Solids Dispersion," Chem. Pharm. Bull., vol. 55(11), pp. 1557-1562 (2007).
Reynolds, "A New Technique for the Production of Spherical Particles," Manufact. Chemist & Aerosol News, pp. 40-43 (Jun. 1970).
Sucker et al., "Pharmazeutische Techologie," pp. 273-283 (1991) with translation.
USP 32, NF 27, "Pancrelipase Delayed-Release Capsules.", (2009).
Benzonana, et al., "Etude Cinetique de L'Action de la Lipase Pancreatique Sur Des Triglycerides en Emulsion Essai D'Une Enzymologie en Milieu Heterogene," Biochimica Et Biophysica ACTA, 105:121-136 (1965) (English Abstract).
Bezzine, et al., "Human Pancreatic Lipase: Colipase Dependence and Interfacial Binding of Lid Domain Mutants," Biochemistry, 23:5499-5510 (1999).
Borgstrom, et al., "Pancreatic Juice Co-Lipase: Physiological Importance," Biochimica Et Biophysica ACTA, 242:509-513 (1971).
Borgstrom, et al., "Pancreatic Lipase and Colipase: Interaction and Effect of Bile Salts and Other Detergents," Eur. J. Biochem, 37:60-68 (1973).
Borgstrom, "Binding of Pancreatic Colipase to Interfaces; Effects of Detergents," FEBS Letters, 71(2):201-204 (1976).
Borgstrom, "On the Interactions Between Pancreatic Lipase and Colipase and the Substrate and the Importance of Bile Salts," Journal of Lipid Research, 16:411-417 (1975).
EP 1931317, Aptalis Pharma S.r.L, Submission of Opponent 02 in Preparation of Oral Proceedings, Aug. 3, 2011.
EP 1931317, Nordmark Arzneimittel GmbH & Co. KG, Submission of Opponent 01 in Preparation of Oral Proceedings, Jul. 20, 2011 (with Translation).
Gargouri, et al., "Studies on the Detergent Inhibition of Pancreatic Lipase Activity," Journal of Lipid Research, 24:1336-1342 (1983).
Saunders, et al., "Lecithin Inhibits Fatty Acid and Bile Salt Absorption from Rat Small Intestine In Vivo," Lipids, 11(12):830-832 (1976).
Ammon, et al., "Effect of Lecithin on Jejunal Absorption of Micellar Lipids in Man and on Their Monomer Activity in vitro," Lipds, 14(4):395-400 (1978).
Jones, et al., "Effects of Exogenous Emulsifiers and Fat Sources on Nutrient Digestibility, Serum Lipids, and Growth Performance in Weanling Pigs," J. Anim Sci., 70:3473-3482 (1992).
Kammlott, et al., "Experiments to Optimize Enzyme Substitution Therapy in Pancreatic Duct-Ligated Pigs," Journal of Animal Physiology and Animal Nutrition, 89:105-108 (2005).
Lukovac, et al., "Gelucire 44/14 Improves Fat Absorption in Rats with Impaired Lipolysis," Biochimica et Biophysica Acta, 1801:665-673 (2010).
O'Doherty, et al., "Role of Luminal Lecithin in Intestinal Fat Absorption," Lipids, 8(5):249-255 (1972).
Overland, et al., "Lecithin in Swine Diets: I. Weanling Pigs," J. Anim Sci, 71:1187-1193 (1993).
Overland, et al., "Effect of Lecithin on the Apparent Ileal and Overall Digestibility of Crude Fat and Fatty Acids in Pigs," J. Anim Sci, 72:2022-2028 (1994).
Tabeling, et al., "Studies on Nutrient Digestibilities (Pre-Caecal and Total) in Pancreatic duct-Ligated Pigs and the Effects of Enzyme Substitution," J. Anim. Physiol, a. Anim. Nutr., 82:251-263 (1999).
Archibald, A.L., "Comparison of the Serum Amylases of Farm Animals," Comp. Biochem. Physiol., vol. 88B (3), pp. 963-968 (1987).
Aquacoat ECD—FMC Biopolymer—Bulletin AECD-30-05/18/97. RS (1997).
Carriere, et al., "Quantitative Study of Disgestive Enzyme Secretion and Gastrointestinal Lipolysis in Chronic Pancreatitis," Clinical Gastroenterology and Hepatology, vol. 3(1), pp. 28-38 (2005).
Chueshov, et al., Industrial Technology of Drugs and Medicine, vol. 2, NFAU Publishing House, pp. 359-363 (2002) [with Translation].
Cunningham, L., "Reactivation of Diethyl p-Nitrophenyl Phosphate-Inhibited α-Chymotrypsin by Hydroxylamine," Journal of Biological Chemistry, vol. 207, pp. 443-458 (1954).
De Fiebre et al. "Elimination of Salmonellae from Animal Glandular Products," Applied Microbiology, vol. 17(3), pp. 344-346 (1969).
Delchier, et al., "Fate of Orally Ingested Enzymes in Pancreatic Insufficiency: Comparison of Two Pancreatic Enzyme Preparations," Aliment. Pharmacol. Therap., vol. 5, pp. 365-378 (1991).
Dimagno, et al., "Fate of Orally Ingested Enzymes in Pancreatic Insufficiency," The New England Journal of Medicine, vol. 296(23), pp. 1318-1322 (1977).
Dutta, et al., "Critical Examination of Therapeutic Efficacy of a pH-Sensitive Enteric-Coated Pancreatic Enzyme Preparation in Treatment of Exocrine Pancreatic Insufficiency Secondary to Cystic Fibrosis," Digestive Diseases and Sciences, vol. 33(10), pp. 1237-1244 (1988).
Enzyme Nomenclature., Recommendations of the Nomenclature Committee of the International Union of Biochemistry and Molecular Biology on the Nomenclature and Classification of Enzymes by the Reactions they Catalyse, available at http://www.chem.qmul.ac.uk/iubmb/enzyme/.
English Abstract of JP 4187085.
Estes, et al., "Proteolytic Enhancement of Rotavirus Infectivity: Molecular Mechanisms," Journal of Virology, vol. 39(3), pp. 879-888 (1981).
European Patent Appl. No. 06778012.2 Office Action dated Dec. 7, 2010 (5 pages).
Fang, et al., "Purification and Characterization of Adult Diarrhea Rotavirus: Identification of Viral Structural Proteins," Journal of Virology, vol. 63(5), pp. 2191-2197 (1989).
Federal Register, vol. 69(82), Part IV, Apr. 28, 2004.
Fiedler, Herbert P. Encyclopedia of Excipients for Pharmaceuticals, Cosmetics and Related Areas, 5th ed., pp. 1284-1287 (2002).
Gregory, P.C., "Gastrointestinal pH, Motility/Transit and Permeability in Cystic Fibrosis," J Pediatr Gastroenterol Nutr, vol. 23(5), pp. 513-523 (1996).
Guarner, et al., "Fate of Oral Enzymes in Pancreatic Insufficiency," Gut, vol. 34, pp. 708-712 (1993).
Hogan et al., Pharmaceutical Coating Technology, Chapter 14, pp. 409-439 (1995).
International Preliminary Report of Patentability for PCT/EP2008/065586 (dated May 18, 2010).
International Search Report for PCT/EP2008/065586 (dated Dec. 19, 2008).
International Search Report PCT/EP2009/050010 (dated May 7, 2009).
Jiang et al., "Biochemical Characterization of the Structural and Nonstructural Polypeptides of a Porcine Group C Rotavirus," Journal of Virology, vol. 64(7), pp. 3171-3178 (1990).
Keller, et al., "Pancreatic Enzyme Supplementation Therpay," Current Treatment Option in Gastroenterology, vol. 6, pp. 369-374 (2003).
Keller, et al., "Human Pancreatic Exocrine Response to Nutrients in Health and Disease," Gut, vol. 54(Suppl. VI), pp. vi1-vi28 (2005).

(56) References Cited

OTHER PUBLICATIONS

Kirk-Othmer, Encyclopedia of Chemical Technology, vol. 23, pp. 724-725 (1984).
Kobayashi, et al., "Susceptibility of Heptitis B Virus to Disinfectants or Heat," Journal of Clinical Microbiology, vol. 20(2), pp. 214-216 (1984).
Korzhavykh, et al., "Tablets and Their Various Forms", Russian Pharmacies, No. 19, pp. 1-5 (2010) [with Translation].
KREON® 25000 (magnified photograph).
KREON® 25000 Gebrauchsinformation (2007), English Translation.
Layer, et al., "Fate of Pancreatic Enzymes During Small Intestinal Aboral Transit in Humans," The American Physiology Society, pp. G475-G480 (1986).
Layer, et al., "Pancreatic Enzymes in Chronic Pancreatitis," International Journal of Pancreatology, col. 15(1), pp. 1-11 (1994).
Maunula, L., "Molecular Epidemiology of Human Rotaviruses—A Study in Genetic Diversity," Academic Dissertation, Haartman Institute, pp. 1-116, Helsinki 2001.
Material Safety Data Sheet, Pancreatin 4X USP (10X), Invitrogen Corp., pp. 1-7 (Rev. Apr. 16, 2005).
Michen, et al., "Isoelectric Points of Viruses," Journal of Applied Microbiology, vol. 109, pp. 388-397 (2010).
Naftitine HCl MSDS (Jun. 23, 2004), available at http://pharmacycide.com/msds/Naftifine_HCL.
Nilsson, et al., "Biosynthesis and morphogenesis of group C rotavirus in swine testicular cells," Arch. Virol., vol. 133, pp. 21-37 (1993).
Notice of Opposition filed of EP1931316.
Notices of Opposition Filed by Nordmark Arzneimittel GmbH & Co. KG and Eurand S.p.A, EP 1931317; Reply of the Patent Proprietor to the Notice of Opposition.
Pharmaceutical Excipients, 5th ed., Cetyl Alcohol, pp. 155-156 (2006).
Register of Pharmaceuticals in Russia, RP-Pharmacist, Annual Collection, Issue 5, p. 772 (2003) [with Translation].
Remington, The Science and Practice of Pharmacy, 20th ed., pp. 326 and 1035-1036 (2000).
Sachs-Barrable, et al., "Lipid Excipients Peceol and Gelucire 44/14 Decrease P-Glycoprotein Mediated Efflux of Rhodamine 123 Partially Due to Modifying P-Glycoprotein Protein Expression within Caco-2 Cells," J Pharm Pharmaceut Sci, vol. 10(3), pp. 319-331 (2007).
Saif et al., "Serial Propagation of Porcine Group C Rotavirus (Pararotavirus) in a Continuous Cell Line and Characterization of the Passaged Virus," Journal of Clinical Microbiology, vol. 26(7), pp. 1277-1282 (1988).
Sanekata, et al., "Isolation of Group B Porcine Rotavirus in Cell Culture," Journal of Clinical Microbiology, vol. 34(3), pp. 759-761 (1996).
Savage et al., "Determination of Adequate Moisture Content for Efficient Dry-Heat Viral Inactivation in Lyophilized Factor VIII Loss on Drying and by Near Infrared Spectroscopy," Biologicals, vol. 26, pp. 119-124 (1998).
Sofer, et al., "Part 6, Inactiviation Methods Grouped by Virus," BioPharm Internationals, S-37-42 (2003).
Sun et al., "Fluidized-bed spray coated porous hydrogel beads for sustained release of diclofenac sodium," Journal of Controlled Release, vol. 47, pp. 247-260 (1997).
The Ministry of Health, Labour and Welfare Ministerial Notification No. 285, Japan Pharmacopoeia, 8 pages (2006).
Thoma et al., "Influence of aqueous coatings on the stability of enteric coated pellets and tablets," European Journal of Pharmaceutics and Biopharmaceutics, vol. 47, pp. 39-50 A286(1999).
Tsunemitsu, et al., "Isolation, Characterization, and Serial Propagation of a Bovine Group C Rotavirus in a Monkey Kidney cell Line (MA104)," Journal of Clinical Microbiology, vol. 29(11), pp. 2609-2613 (1991).
U.S. Appl. No. 11/464,754, filed Aug. 15, 2006, Sep. 2, 2009 Non-Final Office Action.
U.S. Appl. No. 11/464,754, filed Aug. 15, 2006, Feb. 19, 2010 Response to the Sep. 2, 2009 Non-Final Office Action.
U.S. Appl. No. 11/464,754, filed Aug. 15, 2006, Jun. 1, 2010 Final Office Action.
U.S. Appl. No. 11/464,754, filed Aug. 15, 2006, Dec. 1, 2010 Response to the Jun. 1, 2010 Final Office Action.
Walsh, et al., "Tryosinogen and Chymotrypsinogen as Homologous Proteins," PNAS, vol. 52, pp. 884-889 (1964).
Wallis, et al., "Plaque Enhancement of Enteroviruses by Magnesium Chloride, Cysteine, and Pancreatin," Journal of Bacteriology, vol. 91(5), pp. 1932-1935 (1996).
Wan et al., "Plasticizers and their effects on microencapsulation process by spray-drying in an aqueous system," J. Microencapsulation, vol. 9(1), pp. 53-62 (1992).
Watkins, Paul, "The Barrier Function of CYP3A4 and P-Glycoprotein in the Small Bowel," Advanced Drug Delivery Reviews, vol. 27, pp. 161-170 (1997).
Worthington Enzyme Manual, Lipase, (1993), pp. available at http://www.worthington-biochem.com/PL/default.html (2 pages).
Worthington Enzyme Manual, Trypsin (1993), available at http://www.worthington-biochem.com/TRY/default.html (3 pages).
Worthington Enzyme Manual, Trypsinogen (1993), available at http://www.worthington-biochem.com/TG/default.html (1 page).
2.9.1 Disintegration of Tablets and Capsules, European Pharmacopoeia 5.3, pp. 3351-3353 (2006).
Axcan Pharma, Inc., Viokase Prescribing Information, Mar. 2000, 3 pages.
Bieger, W. et al., "Two-dimensional isoelectric focusing/sodium dodecyl sulfate gel electrophoresis of protein mixtures containing active or potentially active proteases analysis of human exocrine pancreatic proteins," Anal. Biochem. (1980) 109:222-230.
Challapalli, K.K. et al., "High reproducibility of large-get two-dimensional electrophoresis," Electrophoresis (2004) 25:3040-3047.
Cunningham, N. et al., "Replication of avian infectious bronchitis virus in African green monkey kidney cell line VERO," J. Gen. Virol. (1972) 16:423-427.
DeRobertis, Cell & Mol. Biol. (1980) 7th Ed., 132-133.
Definition of "picornaviridae," http://medical-dictionary.thefreedictionary.com/Picornaviridae, downloaded Jul. 26, 2011.
Dony, J. et al., "Etide electrophoretique et immunoelectrophoretique de preparations enzymatiques injectables: preparation d'origine pancreatique et preparations d'origine testiculaire," progress in Immunological Standardization (1970) 4:395-405, with English translation.
Fallis, LS. et al., "Observations on some metabolic changes after total pancreatoduodenectomy," Annals of Surgery (1948) 639-667.
"Gastric juice" (http://www.thefreedictionary.com/gastric+juice) accessed Aug. 2, 2013.
Goerg, A et al., "The current state of two-dimensional electrophoresis with immobilized gH gradients," Electrophoresis (2000) 21:1037-1053.
Goldman, D. et al., "Human lymphocyte polymorphisms detected by quantitative two-dimensional electrophoresis," Am. J. Hum. Genet. (1983) 35:827-837.
Goodman & Gilman's "The Pharmacological Basis of Therapeutics," 8th Edition, Pergamon Press (1990) 1471-1477.
Jenkins, L.W. et al., "Conventional and functional proteomics using large formal two-dimensional gel electrophoresis 24 hours after controlled cortical impact in postnatal day 17 rats," J. Neurotrauma (2002) 19(6):715-740.
Klotz, H.P., "Lyophilized pancreatic extract, an aid in the treatment of mild diabetes," La Nouvelle Presse Medicals (1975) 4(32):2333, abstract.
Korneeva, O.S. et al., "Identification of catalytically active groups of wheat (*Triticum aestivum*) germ lipase," Appl. Biochem. & Microbiol. (2008) 44(4):349-355.
Lebowitz, J. et al., "Modern analytical ultracentrifugation in protein science: a tutorial review," Protein Sci. (2002) 11:2067-2079.
May et al., J. Biol. Standardization (1982) 10:249-259.
Meyer, Boyd Anal. Chem. (1959) 31:215-219.

(56) References Cited

OTHER PUBLICATIONS

Murlin et al., "The influence of alkili upon the glycos uria, hyperglycemia and carbon dioxide combining power in human diabetes," Proceedings of the Society for Experimental Biol. Med. (1917) 14:8-9.
Nishihara, J.C. et al., "Quantitative evaluation of proteins in one- and two-dimensional polyacrylamide gels using a fluorescent stain," Electrophoresis (2002) 23:2203-2215.
Padfield, P.J. et al., "The use of two-dimensional gel electrophoresis and high-performance liquid chromatography for the analysis of pancreatic juice," The Pancreas: Biology, Pathbiology, and Disease, Second Edition, Chapter 14 (1993) 265-273.
Pariza, M.W. et al., "Evaluating the safety of microbial enzyme preparations used in food processing: update for a new century," Regul. Toxicol. Pharmacol. (2001) 33(2): 173-186.
Porter, S.C., "Coating of pharmaceutical dosage forms," Chapter 46, Remington: The Science and Practice of Pharmacy, Lippincott, Williams & Wilkins, Philadelphia (2005) 21st Edition, Chapter 46:929-938.
Reed, L.J. et al., "A simple method of estimating fifty percent end points," Amer J. of Hygiene (1938) 27(3):493-497.
Ridder, G. et al., "Quantitative analysis of pattern recognition of two-dimensaional electrophoresis gels," Clin. Chem. (1984) 30(12): 1919-1924.
Scharpe, S. et al., "Isoelectric characterization of porcine pancreative alpha amylases," Journal De Pharmacie De Belgique (1973) 28(6):705-708.
Scheele, G.A., "Two-dimensional gel analysis of soluble proteins," J. Biol. Chem. (1975) 250(14):5375-5385.
Shimura, K. et al., "Affinophoresis in two-dimensional agarose gel electrophoresis specific separation of biomolecules by a moving affinity ligand," Anal. Biochem. (1987) 161(1):200-206.
Smolka, M. et al., "Quantitative protein profiling using two-dimensional gel electrophoresis, isotope-coded affinity tag labeling, and mass spectrometry," Mol. Cell Proteomics (2002) 1.1:19-29.
Spearman, C., "The method of 'right and wrong cases' ('constant stimuli') without Gauss's formulae," Brit. J. Psych. (1908) vol. II, Part 3, 227-242.
United States Pharmacopoeia for Pancrelipase Delayed-Release Capsules (2 pages) (2006).
Van Den Bergh, G. et al., "Fluorescent two-dimensional difference gel electrophoresis and mass spectrometry identify age-related protein expression differences for the primary visual cortex of kitten and adult cat," J. Neurochem. (2003) 85:193-205.
Veronese et al., "Photo inactivation of enzymes by linear and angular furocoumarins," Photochem & Photobiol. (1982) 36(1):25-30.
Villegas et al., "A rapid method to produce high yields of purified rotavirus particles," J. Virol. Meth. (2002) 104:9-19.
Voss, T. et al., "Observations on the reproducibility and matching efficiency of two-dimensional electrophoresis gels: consequences for comprehensive data analysis," Electrophoresis (2000) 21:3345-3350.
European Patent Office Search Report and Opinion for Application No. 07120740.1 dated Mar. 1, 2008.
European Patent Office Search Report for Application No. 10178590 dated Dec. 9, 2010.
European Patent Office Search Report and Preliminary Opinion for Application No. 06114329 dated Aug. 1, 2006.
European Search Report for Application No. 07120740.1 dated Mar. 3, 2008.
European Search Report for Application No. 97114330 dated Jun. 5, 2002.
International Preliminary Report on Patentability for Application No. PCT/EP2004/008332 dated Jan. 30, 2006.
International Search Report and Written Opinion for Application No. PCT/EP2005/051295 dated Jun. 24, 2005.
International Search Report for Application No. PCT/EP2004/008332 dated Nov. 24, 2004.
International Search Report for Application No. PCT/EP2007/054880 dated Sep. 18, 2007.
Written Opinion for Application No. PCT/EP2007/054880 dated Sep. 18, 2007.
United States Patent Office Action for U.S. Appl. No. 11/464,754 dated Aug. 16, 2013 (26 pages).
United States Patent Office Action for U.S. Appl. No. 11/085,073 dated Oct. 23, 2006 (12 pages).
United States Patent Office Action for U.S. Appl. No. 11/085,073 dated Jul. 13, 2007 (13 pages).
United States Patent Office Action for U.S. Appl. No. 11/085,073 dated Apr. 7, 2008 (17 pages).
United States Patent Office Action for U.S. Appl. No. 11/085,073 dated Feb. 26, 2010 (19 pages).
United States Patent Office Action for U.S. Appl. No. 11/460,330 dated Nov. 12, 2010 (13 pages).
United States Patent Office Action for U.S. Appl. No. 11/460,330 dated Aug. 4, 2011 (21 pages).
United States Patent Office Action for U.S. Appl. No. 11/460,330 dated Apr. 9, 2012 (21 pages).
United States Patent Office Action for U.S. Appl. No. 11/751,497 dated Nov. 12, 2009 (12 pages).
United States Patent Office Action for U.S. Appl. No. 11/751,497 dated Jul. 14, 2010.
United States Patent Office Action for U.S. Appl. No. 11/751,497 dated Mar. 10, 2011 (8 pages).
United States Patent Office Action for U.S. Appl. No. 11/751,497 dated Apr. 17, 2013 (16 pages).
United States Patent Office Action for U.S. Appl. No. 12/271,480 dated Nov. 3, 2010.
United States Patent Office Action for U.S. Appl. No. 12/271,480 dated Jul. 14, 2011 (12 pages).
United States Patent Office Action for U.S. Appl. No. 12/271,480 dated May 24, 2013 (14 pages).
United States Patent Office Action for U.S. Appl. No. 12/271,480 dated Sep. 19, 2013 (13 pages).
Copending U.S. Appl. No. 14/074,255, filed Nov. 7, 2013.
Brewer et al., "Porcine encephalomyocarditis virus persists in pig myocardium and infects human myocardial cells," J. Virology (2001) 75(23):11621-11629.
McLean et al., "Contamination detection in animal cell culture," Encyclopedia of Cell Technology (2000) 1-2:586-598.
United States Patent Office Action for U.S. Appl. No. 11/460,330 dated Oct. 18, 2013 (22 pages).
United States Patent Office Action for U.S. Appl. No. 11/751,497 dated Oct. 21, 2013 (13 pages).
U.S. Patent Office Action for U.S. Appl. No. 11/464,754 dated Apr. 23, 2014 (31 pages).
U.S. Patent Office Notice of Allowance for U.S. Appl. No. 11/085,073 dated Apr. 1, 2014 (17 pages).
U.S. Patent Office Action for U.S. Appl. No. 11/460,330 dated Jun. 2, 2014 (23 pages).
U.S. Appl. No. 60/708,526 by George Shlieout et al., filed Aug. 15, 2005.
Biswal, S. et al, "Production variables affecting characteristics of pellets in melt pellitization with wax combination in a laboratory scale spheronizer," Acta Pharm. (2009) 59:199-210.
Loa, C.C. et al., "Purification of turkey coronavirus by stephacryl size-exclusion chromatography," J. Virol. Meth. (2002) 104:187-194.
Mesiha, M.S. et al., "A screening study of lubricants in wet powder masses suitable for extrusion-spheronization," Drug Dev. & Ind. Pharm. (1993) 19(8):943-959.
PEG 4000, EM Grade, Technical Data Sheet 279, Polysciences, Inc. (1999) 2 pages.
ShinEtsu Chemical Company, USP Hypromellose Phthalate Enteric Coating Material (Sep. 2002) 10 pages.
Tabasi, S.H. et al., "Quality by design, Part I: Application of NIR spectroscopy to monitor tablet manufacturing process," J. Pharm. Sci. (2008) 97:4040-4051.
Tabasi, S.H. et al., "Quality by design, Part II: Application of NIR spectroscopy to monitor the coating process for a pharmaceutical sustained release product," J. Pharm. Sci. (2008) 97:4052-4066.

(56) References Cited

OTHER PUBLICATIONS

Tabasi, S.H. et al., "Quality by design, Part III: Study of curing process of sustained release coated products using NIR spectroscopy," J. Pharm. Sci. (2008) 97:4067-4086.
Ueba, O., "Respiratory synctial virus. I. Concentration and purification of the infectious virus," Acta Medica Okayama (1978) Article 2, 32(4):265-272.
U.S. Pharmacopeia 28, National Formulary 23, 23rd Edition, (2004) 10 pages.
United States Patent Office Action for U.S. Appl. No. 12/271,480 dated Jan. 6, 2015 (15 pages).
Aptalis Farma S.r.L., Certificate of Inscription in the Regular Identification Data of the Company (Jul. 15, 2011) 4 pages.
Decision to Revoke the European Patent No. EP1931317 in the Opposition filed by Nordmark against European Patent No. 1931317 dated Nov. 17, 2011.
Die Tablette, Handbuch der Entwicklung, Herstellung und Qualitatssicherung, Editiv cantor Verlag Aulendorf (2002) Seiten 85-89, 91-106, 583,584, W.A. Ritschel eds.
Grounds of Appeal in the Opposition filed by Aptalis Pharma S.r.L. against European Patent No. 1931316 dated Jan. 2, 2013.
Grounds of Appeal in the Opposition filed by Nordmark against European Patent No. 1931317 dated Mar. 15, 2012.
Pharmazeutische Technologie, Georg Thieme Verlag Stuttgart (1978/1991) 2:178-179.
Reply from Opponent in the Opposition filed by Nordmark against European Patent No. 1931317 dated Jul. 20, 2012.
Reply of Proprietor in the Opposition filed by Aptalis Pharma S.r.L. against European Patent No. 1931316 dated Jun. 7, 2011.
Reply to Appeal in the Opposition filed by Nordmark Against European Patent No. 1931317 dated Sep. 28, 2012.
Reply to Appeal in the Opposition filed by Aptalis Pharma S.r.L. against European Patent No. 1931316 dated May 13, 2013.
Reply to Summons to Attend Oral Proceedings: filing of new main claim request in the Opposition filed by Aptalis Pharma S.r.L. against European Patent No. 1931316 dated Feb. 23, 2012.
Reply to Summons to Attend Oral Proceedings: New Written Submissions and Claim Amendments in the Opposition filed by Nordmark against European Patent No. 1931317 dated Aug. 4, 2011.
Results and Minutes of Oral Proceedings in the Opposition filed by Aptalis Pharma S.r.L. against European Patent No. 1931316 dated Sep. 5, 2012.
Results and Minutes of Oral Proceedings in the Opposition filed by Nordmark against European Patent No. 1931317 dated Oct. 6, 2011.
Rompp Chemie Lexikon, Jurgen Falbe et al. editors, (1992) Georg Thieme Verlag, 9:3532 "Polyethylenglykole".
Summons to Oral Proceedings in the Opposition filed by Aptalis Pharma S.r.L. against European Patent No. 1931316 dated Dec. 22, 2011.
Summons to Oral Proceedings in the Opposition filed by Nordmark Arzneimittel GmbH against European Patent No. 1931317 dated Mar. 29, 2011.
Technical Reports on Comparative Exp.x, examples 1/7 thru 7/7 (2009), including B810586 "PEG4000 iprop high"; B810587 "PEG2000"; B810588 "PEG8000"; B810589 "HPMC iprop equ"; B810590 "PVP iprop equ"; B810591 "HPMC iprop high"; and B810592 "PVP iprop low".
Written Submission in the Opposition filed by Nordmark against European Patent No. 1931317 dated Aug. 25, 2011.
Written Submission by Aptalis Pharma S.r.L. in the Opposition filed by Aptalis Pharma S.r.L. against European Patent No. 1931316 dated Mar. 12, 2012.
Written Submission by Opponent in the Opposition filed by Aptalis Pharma S.r.L. against European Patent No. 1931316 dated May 4, 2012.
United States Patent Office Action for U.S. Appl. No. 11/460,330 dated Sep. 24, 2015 (39 pages).

Die Tablette, Handbuch der Entwicklung, Herstellung und Qualitatssicherung, Editiv cantor Verlag Aulendorf (2002) Seiten 85-89, 91-106, 583,584, W.A. Ritschel eds. with English translation.
Pharmazeutische Technologie, Georg Thieme Verlag Stuttgart (1978/1991) 2:178-179, with English translation.
Reply from Opponent in the Opposition filed by Nordmark against European Patent No. 1931317 dated Jul. 20, 2012, with English translation.
Rompp Chemie Lexikon, Jurgen Falbe et al. editors, (1992) Georg Thieme Verlag, 9:3532 "Polyethylenglykole", with English translation.
Written Submission in the Opposition filed by Nordmark against European Patent No. 1931317 dated Aug. 25, 2011, with English translation.
United States Patent Office Action for U.S. Appl. No. 11/460,330 dated Jun. 5, 2015 (38 pages).
United States Patent Office Action for U.S. Appl. No. 11/751,497 dated May 22, 2015 (12 pages).
United States Patent Office Notice of Allowance for U.S. Appl. No. 12/271,480 dated Jul. 20, 2015 (13 pages).
United States Patent Office Notice of Allowance for U.S. Appl. No. 11/464,754 dated Jul. 27, 2015 (17 pages).
Sottong et al., "Recovery of murine leukemia virus from large volumes of freshly harvested culture fluids by using a single density gradient," Applied Microbiology, vol. 29, No. 1, Jan. 1975, p. 102-105.
USPTO Office Action for U.S. Appl. No. 11/751,497, dated Nov. 13, 2015.
USPTO Office Action for U.S. Appl. No. 11/751,497, dated Feb. 22, 2016.
USPTO Office Action for U.S. Appl. No. 12/271,480, dated Mar. 24, 2016.
USPTO Office Action for U.S. Appl. No. 11/751,497, dated Oct. 7, 2016.
Buhler, V., Polyvinylpyrrolidone Excipients for Pharmaceuticals, Povidone, Crospovidone and Copovidone (2005) 1-254, Springer-Verlag.
Luwa, http://www.icicorp.com/industrial_granulation, accessed Dec. 16, 2015.
Rudric, E.M. et al., "Oral solid dosage forms," Remington: The Science and Practice of Pharmacy, 21st Edition (2005) Chapter 45, 889-928.
United States Patent Office Action for U.S. Appl. No. 11/751,497 dated Nov. 13, 2015 (16 pages).
USPTO Non-Final Office Action for U.S. Appl. No. 11/085,073 dated Mar. 13, 2014 (15 pages).
USPTO Non-Final Office Action for U.S. Appl. No. 14/308,543 dated Jan. 19, 2017 (14 pages).
USPTO Final Office Action for U.S. Appl. No. 14/308,543 dated Nov. 14, 2017 (16 pages).
USPTO Non-Final Office Action for U.S. Appl. No. 14/308,543 dated Jul. 12, 2018 (7 pages).
USPTO Non-Final Office Action for U.S. Appl. No. 15/214,973 dated Mar. 22, 2018 (24 pages).
USPTO Notice of Allowance for U.S. Appl. No. 11/464,754 dated Oct. 30, 2015 (9 pages).
USPTO Notice of Allowance for U.S. Appl. No. 14/882,385 dated Feb. 24, 2016 (13 pages).
USPTO Final Office Action for U.S. Appl. No. 11/751,497 dated Jun. 7, 2017 (14 pages).
USPTO Non-Final Office Action for U.S. Appl. No. 11/751,497 dated Sep. 27, 2017 (7 pages).
USPTO Notice of Allowance for U.S. Appl. No. 11/751,497 dated May 9, 2018 (12 pages).
USPTO Final Office Action for U.S. Appl. No. 12/271,480 dated Oct. 5, 2016 (11 pages).
USPTO Non-Final Office Action for U.S. Appl. No. 12/271,480 dated Nov. 2, 2017 (11 pages).
USPTO Final Office Action for U.S. Appl. No. 12/271,480 dated May 31, 2018 (14 pages).
Creon, Prescribing Information, Initial U.S. Approval: 2009, 20 pages.

(56) References Cited

OTHER PUBLICATIONS

Pancreaze, Prescribing Information, Initial U.S. Approval: 2010, 21 pages.
Pertzye, Prescribing Information, Initial U.S. Approval: 2012, 11 pages.
Ultresa, Prescribing Information, Initial U.S. Approval: 2012, 13 pages.
Viokace, Prescribing Information, Initial U.S. Approval: 2012, 8 pages.
Zenpep, Prescribing Information, Initial U.S. Approval: 2009, 20 pages.
Tony Trang, Johanna Chan, David Y Graham, Pancreatic enzyme replacement therapy for pancreatic exocrine insufficiency in the 21st century, World Journal of Gastroenterology, Sep. 7, 2014; 20(33): 11467-11485.
United States Pharmacopoeia Method 711 Dissolution, Apr. 1, 2006, 18 pages.
Prosecution File History for EP Patent No. 1335706, 1336 pages. Retrieved Apr. 17, 2021 from https://register.epo.org/application?number=EP01994654&d-16544-o=2&lng=en&tab=doclist&d-16544-s=1.
Translation of "Supplementary expert opinion for submission to the European Patent Office" filed Sep. 30, 2011 for EP Patent No. 1335706, 3 pages.

\* cited by examiner

PROCESS FOR THE MANUFACTURE AND USE OF PANCREATIN MICROPELLET CORES

CROSS-REFERENCE TO RELATED APPLICATIONS

This application claims the benefit of U.S. Provisional Application Nos. 60/708,526 and 60/708,692 which were both filed Aug. 15, 2005 and are both hereby incorporated by reference.

FIELD OF THE INVENTION

A process for the manufacture and use of a medicament containing pancreatin is described herein. More specifically, processes for manufacturing pancreatin micropellet cores which are substantially free of synthetic oils are described. Also described herein are pancreatin micropellets which are enteric-coated pancreatin micropellet cores.

BACKGROUND

Pancreatin microspheres are the treatment of choice for diseases or disorders caused by digestive enzyme deficiency in mammals such as humans. This is due to the fact that high-performance pancreatin microsphere products like Creon™ provide a therapeutically effective load of active enzymes while at the same time providing properly sized microspheres capable of targeting the optimal location in the digestive tract where digestive enzyme activity will be needed, in particular the upper intestine.

Recently, governmental health authorities have initiated a reassessment of the compatibility of certain pharmaceutical excipients which had previously been used in the formulation of pancreatin-containing products and have provided advice concerning specific pharmaceutical excipients (see e.g. US Code of Federal Regulations, 21 CFR § 201.302), such as mineral oil. It is recommended today that mineral oil not be provided indiscriminately to either pregnant women or infants. Thus, there is a need provide patients with a pancreatin micropellet product in compliance with the current advice of the health authorities and which does not include synthetic oils such as mineral oil.

The use of synthetic oils like paraffins, e.g. liquid paraffins (mineral oils), in particular highly liquid paraffin (light mineral oil) has previously been understood to be a necessary excipient for manufacturing pancreatin micropellet products by extrusion and subsequent spheronisation of the extrudates. One example is described in document EP 0 583 726 (U.S. Pat. No. 5,378,462), which discloses pancreatin micropellets and their preparation with polyethylene glycol 4000, paraffin and a lower alcohol, by extrusion and subsequent spheronisation.

United States Pat. App. No. 2004/0101562 (Maio) discloses microspheres of pancreatic enzymes with high stability and a production method thereof. A solid mixture, including one or more pancreatic enzymes, one or more hydrophilic low-melting polymers and other excipients, is heated at a temperature equal or higher than the melting temperature of said hydrophilic low-melting polymer while stirring. However, Maio emphasizes that a fundamental feature of the process described therein is the total absence of any solvents, either water or other organic solvents.

In United States Pat. App. No. 2002/0061302 a method for the treatment of diabetes by administering a physiologically acceptable enzyme mixture having lipolytic, proteolytic and amylolytic activity to a patient in need thereof is described.

US patent application No. 2004/0213847 relates to delayed pharmaceutical compositions containing proton pump inhibitors.

U.S. Pat. No. 4,786,505 teaches pharmaceutical preparations for oral use.

Further pharmaceutical preparations which may comprise pancreatin and an enteric coating are e.g. known from documents DE 19907764; EP 0 021 129 (U.S. Pat. No. 4,280,971); EP 0 035 780; U.S. Pat. Nos. 5,225,202; 5,750,148; 6,224,910; U.S. Pat. App. No. 2002/0146451 or WO 02/40045.

SUMMARY

Accordingly, one embodiment disclosed herein is a process for making and using pancreatin micropellet cores which are substantially free of synthetic oils. Another embodiment provides pancreatin micropellets substantially free of synthetic oils which are enteric-coated pancreatin micropellet cores.

Another embodiment provides a method of treating various medical conditions such as pancreatic exocrine insufficiency, pancreatitis, cystic fibrosis, diabetes type I and diabetes type II by using the pancreatin micropellet cores and/or pancreatin micropellets obtained by the processes described herein.

Another embodiment provides a pharmaceutical composition in an oral dosage form containing a pharmacologically effective amount of pancreatin wherein the pancreatin is in the form of pancreatin micropellet cores and/or pancreatin micropellets manufactured according to the processes described herein.

Other objects, features and advantages will be set forth in the detailed description of the embodiments that follows, and in part will be apparent from the description or may be learned by practice of the claimed invention. These objects and advantages will be realized and attained by the processes and compositions particularly pointed out in the written description and claims hereof.

DETAILED DESCRIPTION

While the present invention is capable of being embodied in various forms, the description below of several embodiments is made with the understanding that the present disclosure is to be considered as an exemplification of the invention, and is not intended to limit the invention to the specific embodiments illustrated. The headings used through-out this disclosure are provided for convenience only and are not to be construed to limit the invention in any way. Embodiments illustrated under any heading may be combined with embodiments illustrated under any other heading.

Pancreatin is a mixture of different physiologically active endogenous ingredients which are derived from mammalian pancreas glands and comprised of several different digestive enzymes such as lipases, amylases and proteases. Mammalian pancreatic lipase is a valuable digestive enzyme supplement for the treatment of various medical conditions such as pancreatic exocrine insufficiency. However, pancreatic proteases and amylases also contribute to the therapeutic value of pancreatin. Pancreatin for pharmaceutical use is typically of bovine or porcine origin with porcine pancreatin being preferred.

It has now been surprisingly found that pancreatin micropellet cores which are suitable for enteric coating, are high in enzymatic activity and are substantially free of synthetic oils like paraffins, e.g. highly liquid paraffin, can be produced by the processes described herein. It has further been found that the manufacturing process described herein is an improvement when compared to known processes which use mineral oil or known processes which would e.g. need more process steps to produce pancreatin micropellet cores.

In particular, pancreatin micropellet cores can be produced by the process described herein which comprise about 10% to about 95% by weight of pancreatin, about 5% to about 90% by weight of at least one pharmaceutically acceptable binding agent and 0% to about 10% by weight of at least one pharmaceutically acceptable excipient. More specifically, pancreatin micropellet cores can be produced by the process described herein which comprise about 70% to about 90% by weight of pancreatin, about 10% to about 30% by weight of at least one pharmaceutically acceptable binding agent and 0% to about 5% by weight of at least one pharmaceutically acceptable excipient. In one embodiment, pancreatin micropellet cores can be produced which comprise about 70% to about 90% by weight pancreatin, and about 10% to about 30% by weight of at least one pharmaceutically acceptable binding agent.

For the purposes of the present disclosure, the prefix "micro" used to describe a micropellet or a microsphere means that the diameter or each of the individual dimensions (length, height, width) is equal to or less than about 5 mm. Producing pancreatin micropellet cores which are approximately spherical and have a diameter of 0.5 to 2.0 mm is preferred.

The term "synthetic oils" means unsaponifiable hydrocarbons or mixtures of hydrocarbons and comprises e.g. liquid and solid paraffins, in particular liquid paraffins (mineral oils), more particularly highly liquid paraffin (light mineral oil).

The phrase "substantially free of synthetic oils" means that the manufacturing processes described herein and used to make the pancreatin micropellet cores and/or pancreatin micropellets do not utilize one or more synthetic oils as an excipient although synthetic oils may be present as pharmaceutically acceptable trace contaminants in the pancreatin, binding agent(s), enteric coating constituents, the enzyme-friendly organic solvents and/or excipients which are used to manufacture the pancreatin micropellet cores and/or pancreatin micropellets described herein.

One embodiment described herein is a process for the manufacture of pancreatin micropellet cores, comprising the steps of:
a. preparing an extrudable mixture comprising:
   i. about 10% to about 95% pancreatin;
   ii. about 5% to about 90% of at least one pharmaceutically acceptable binding agent;
   iii. 0% to about 10% of at least one pharmaceutically acceptable excipient; and
   iv. one or more enzyme-friendly organic solvents in an amount sufficient to form an extrudable mixture;
   wherein the percentages of components are weight to weight of the pancreatin micropellet cores;
b. creating pancreatin micropellet cores from the extrudable mixture;
c. forming the pancreatin micropellet cores into approximately spherical or approximately ellipsoidal shape in the presence of additional enzyme-friendly organic solvent; and
d. removing the one or more enzyme-friendly organic solvents from the pancreatin micropellet cores such that the pancreatin micropellet cores are substantially free of the one or more enzyme-friendly organic solvents;
wherein the pancreatin micropellet cores are substantially free of synthetic oils.

Examples of pharmaceutically acceptable binding agents include polyethylene glycol 1500, polyethylene glycol 2000, polyethylene glycol 3000, polyethylene glycol 4000, polyethylene glycol 6000, polyethylene glycol 8000, polyethylene glycol 10000, hydroxypropyl methylcellulose, polyoxyethylen, copolymers of polyoxyethylen-polyoxypropylen and mixtures of said organic polymers. The foregoing list of pharmaceutically acceptable binding agents is not meant to be exhaustive, but merely illustrative as a person or ordinary skill in the art would understand that many other pharmaceutically acceptable binding agents or combination of binding agents could also be used. Polyethylene glycol 4000 is the preferred pharmaceutically acceptable binding agent. For the purposes of the present disclosure, synthetic oils are not to be regarded as suitable pharmaceutically acceptable binding agents.

Examples of suitable pharmaceutically acceptable excipients include gliding agents like magnesium stearate or calcium stearate, stearic acid, talcum and/or starch; fillers like calcium phosphate, corn starch, dextrans, dextrin, hydrated silicon dioxide, microcrystalline cellulose, kaolin, lactose, mannitol, polyvinyl pyrrolidone, precipitated calcium carbonate, sorbitol and/or talcum; disintegrating agents like Aerosil™ (silicic acid), alginic acid, amylose, calcium alginate, calcium carbonate, formaldehyde gelatin, pectic carbonate, sago starch, sodium bicarbonate and/or starch; and/or moisturizers like glycerol and/or starch. The foregoing list of pharmaceutically acceptable excipients is not meant to be exhaustive, but merely illustrative as a person or ordinary skill in the art would understand that many other pharmaceutically acceptable excipients or combination of excipients could also be used. For the purposes of the present disclosure, synthetic oils are not to be regarded as suitable pharmaceutically acceptable excipients. In one embodiment, the pancreatin micropellet cores contain no pharmaceutically acceptable excipients but can optionally contain a higher load or dose of pancreatin.

Process variations wherein the pharmaceutically acceptable excipients are present in an amount of 0% are preferred.

Enzyme-friendly organic solvents facilitate mixing and other processing procedures and may afterwards be removed, for example, by drying. Typically, after removal of the enzyme-friendly organic solvents, a certain amount of solvent remains in the pancreatin micropellet cores. The remaining solvent in the micropellet cores can comprise enzyme-friendly organic solvents, water, or a mixture of enzyme-friendly organic solvents with water. If water is present as a solvent, this will typically have been present in the pancreatin which was used as the starting material. The amount of solvent present in the pancreatin micropellet cores after removal of the enzyme-friendly organic solvents is typically less than about 5% and normally less than about 3% by weight of the pancreatin micropellet core.

Examples of suitable enzyme-friendly organic solvents are acetone, chloroform, dichloromethane or straight-chained or branched $C_{1-4}$-alcohols, particularly methanol, ethanol, 1-propanol, 2-propanol, 2-butanol, tert-butanol or mixtures of said solvents. 2-propanol is the preferred enzyme-friendly organic solvent. For the purposes of the present disclosure, synthetic oils are not to be regarded as suitable enzyme-friendly organic solvents. The enzyme-friendly organic solvent is typically used in an amount of about 15% to about 35% by weight, preferably of about 20% to about 30% by weight, relative to the amount of pancreatin used. The foregoing list of suitable enzyme-friendly organic solvents is not meant to be exhaustive, but merely illustrative as a person or ordinary skill in the art would understand that many other enzyme-friendly organic solvents or combination of solvents could also be used.

The amounts of pancreatin, pharmaceutically acceptable binding agent(s), pharmaceutically acceptable excipient(s) and/or enzyme-friendly organic solvent may be varied by those skilled in the art to arrive at the pancreatin micropellet cores having the preferred composition and characteristics as indicated herein.

The term "substantially free of enzyme-friendly organic solvents" means that the quantity of enzyme-friendly organic solvents present in the pancreatin micropellet cores would be less than about 5% by weight of the pancreatin micropellet core.

Removal of the one or more enzyme-friendly organic solvents from the pancreatin micropellet cores in process step d.) means that said pancreatin micropellet cores are subject to conditions whereby the micropellet cores become substantially free from enzyme-friendly organic solvents. Removal of the enzyme-friendly organic solvents can be by any method known to those of ordinary skill in the art. The preferred method is by drying. Additionally, removal of the one or more enzyme-friendly organic solvents would also typically result in the pancreatin micropellet cores containing an amount of water which is less than about 5% and typically less than about 3% by weight of the pancreatin micropellet core.

In one embodiment, the pancreatin micropellet cores are created in process step b.) by extrusion. Remarkably, an extrudable mixture is obtained even though the mixture is substantially free of synthetic oils. In process step b.), if the creating of the micropellet cores from the extrudable mixture is accomplished by means of extrusion, then the temperature preferably does not exceed about 70° C. during extrusion, more preferably the temperature does not exceed about 50° C. Also, in the event of extrusion, piercing dies are preferably used which have a hole diameter of about 0.5 mm to about 2.0 mm, preferably of about 0.7 mm to about 1.5 mm, e.g. 0.8 mm. If the extrudable mixture is extruded, then the extrudate fragments are brought to a suitable length for the forming step. This can be done e.g. by means of a cutting device arranged downstream to the extruding press in a manner known to a person of ordinary skill in the art. The forming in process step c.) can be carried out e.g. in a customary rounding apparatus, for example a commercially available spheronizer. In the rounding apparatus, the extrudate fragments are then formed into an approximately spherical or approximately ellipsoidal shape in the presence of additional enzyme-friendly organic solvent which may be the same or different than the enzyme-friendly organic solvent used in process step a).

When prepared as described herein (substantially free of synthetic oils), processing of the extrudate fragments in the rounding apparatus is improved relative to other known processes. For example, a lower amount of enzyme-friendly organic solvent needs to be added when forming the pancreatin micropellet cores into an approximately spherical or approximately ellipsoidal shape and fewer of the extrudate fragments stick to parts of the rounding apparatus when the process is practiced with an extruder and rounding apparatus.

A further embodiment comprises pancreatin micropellets which are enteric-coated pancreatin micropellet cores. For enteric coating, any enteric coating can be used which is suitable for delivery of the pancreatin micropellet cores to the upper intestine and compatible with the pancreatin micropellet cores. Examples are enteric coatings known from U.S. Pat. No. 5,378,462 or commercially available enteric coatings like Eudragit™ polymers. Preferred enteric coatings are ones that would not require the presence of synthetic oils.

It has been found that the pancreatin micropellet cores and the pancreatin micropellets produced according to the processes disclosed herein and not using synthetic oils unexpectedly show essentially the same properties as pancreatin micropellet cores and pancreatin micropellets produced according to known processes using mineral oil such as the processes disclosed in U.S. Pat. No. 5,378,462. In particular, the pancreatin micropellet cores and the pancreatin micropellets produced without using synthetic oils have a similar particle size distribution, bulk density and are obtained in similar yields as the pancreatin micropellet cores and pancreatin micropellets produced according to processes which use synthetic oils. Further, the pancreatin micropellet cores produced without using synthetic oils, when compared to similar pancreatin micropellets using synthetic oils, show similar appearances in their surface structures and a similar performance when coated with an enteric coating to give pancreatin micropellets.

In another embodiment, the enteric coating on the pancreatin micropellet cores comprises:
  i) at least one film-forming agent;
  ii) at least one plasticizer; and
  iii) optionally at least one anti-sticking agent.

In one embodiment the enteric coating comprises between about 20% and about 30% by weight, more preferably between about 22% and about 26% by weight, yet more preferably between about 22.5% and about 25% by weight of the total composition of the pancreatin micropellet.

Film-forming agent(s), plasticizer(s) and anti-sticking agent(s) (when present) as used for preparing the enteric coating are hereinafter commonly referred to as "non-solvent coating constituents".

Suitable film-forming agents include agar, Carbopol™ (carbomer) polymers (i.e. high molecular weight, cross-linked, acrylic acid-based polymers), carboxymethyl cellulose, carboxymethylethyl cellulose, carrageen, cellulose acetate phthalate, cellulose acetate succinate, cellulose acetate trimelliate, chitin, corn protein extract, ethyl cellulose, gum arabic, hydroxypropyl cellulose, hydroxypropylmethyl acetate succinate, hydroxypropyl methylcellulose acetate succinate, hydroxypropyl methylcellulose phthalate, methacrylic acid-ethyl methacrylate-copolymer, methyl cellulose, pectin, polyvinyl acetate phthalate, polivinyl alcohol, shellac, sodium alginate, starch acetate phthalate and/or styrene/maleic acid copolymer or mixtures of said film-forming polymers. Cellulose acetate phthalate, hydroxypropyl methylcellulose acetate succinate and/or methacrylic acid-ethyl methacrylate-copolymer are the preferred film-forming agents. Most preferred is hydroxypropyl methylcellulose phthalate, e.g. HP 55 or HPMCP HP-50. Synthetic oils are not to be regarded as preferred film-forming agents. The foregoing list of film-forming agents is not meant to be exhaustive but merely illustrative, as a person or ordinary skill in the art would understand that many other film-forming agents or combination of film-forming agents could also be used.

The plasticizer(s) may generally be present in an amount greater than about 1.5%, and typically in an amount of about 2% to about 20% by weight, relative to the film-forming agent. The plasticizer may contain saturated linear monohydric alcohols having 12 to 30 carbon atoms. More specifically, acceptable plasticizers include lauryl alcohol, tridecyl alcohol, myristyl alcohol, pentadecyl alcohol, cetyl alcohol, heptadecyl alcohol, stearyl alcohol, nonadecyl alcohol, arachic alcohol, behenyl alcohol, carnaubyl alcohol, ceryl alcohol, corianyl alcohol, melissyl alcohol, acetyl tributyl citrate, dibutyl sebacate, fatty acid esters of glycerol, glycerol, polyethylene glycol, propyleneglycol, sorbitan fatty acids, triacetin, triethyl citrate and mixtures of said plasticizers. Preferred plasticizers are cetyl alcohol, stearyl alcohol, triethyl citrate and mixtures thereof. When cetyl alcohol is used as a single plasticizer, it may be present in an amount of greater than about 1.5%, typically in an amount of about 2% to about 15%, preferably about 2% to about 10%, by weight relative to the film-forming agent. When triethyl citrate is used as a single plasticizer, it may be present in an amount of about 5% to about 20%, preferably about 12% to about 15%, by weight relative to the film-forming agent. Synthetic oils are not to be regarded as preferred plasticizers. The foregoing list of plasticizers is not meant to be exhaustive but merely illustrative, as a person or ordinary skill in the art would understand that many other plasticizers or combination of plasticizers could also be used.

In one embodiment the plasticizer is comprised of cetyl alcohol and triethyl citrate which are collectively present in an amount of greater than about 3%, typically in an amount of about 4% to about 20%, in particular between about 6% and about 15%, more particularly between about 7% and about 10%, by weight in relation to the film-forming agent. When the plasticizer is comprised of both cetyl alcohol and triethyl citrate, the weight to weight ratio of cetyl alcohol to triethyl citrate may be from about 0.05:1 to about 1:1, for example 0.1:1, 0.2:1, 0.3:1, 0.4:1, 0.5:1, 0.6:1, 0.7:1, 0.8:1 or 0.9:1. In particular, the ratio of cetyl alcohol to triethyl citrate in said mixture of cetyl alcohol and triethyl citrate may be from about 0.25:1 to about 0.5:1, preferably from about 0.3:1 to about 0.45:1, more preferably from about 0.35:1 to about 0.4:1, and even more preferably from about 0.38:1 to about 0.4:1 (w/w).

The enteric coating optionally comprises an anti-sticking agent. Suitable anti-sticking agents include dimethicone and castor oil. Dimethicone, in particular dimethicone 1000, is the preferred anti-sticking agent. The amount of anti-sticking agent (if present) in the enteric coating is between about 1.5% and about 3% by weight relative to the film-forming agent. Synthetic oils are not to be regarded as preferred anti-sticking agents. The foregoing list of anti-sticking agents is not meant to be exhaustive but merely illustrative, as a person or ordinary skill in the art would understand that many other anti-sticking agents or combination of anti-sticking agents could also be used.

Additional embodiments are also located in U.S. patent application Ser. No. 11/464,754 filed on Aug. 15, 2006 and claiming the benefit of U.S. Provisional Application Nos. 60/708,526 and 60/708,692 which were both filed on Aug. 15, 2005. U.S. patent application Ser. No. 11/464,754 is herein incorporated by reference.

Another embodiment provides a process for the manufacture of pancreatin micropellets, comprising the steps of:
aa. providing pancreatin micropellet cores wherein the pancreatin micropellet cores are substantially free of synthetic oils;
bb. providing an enteric-coating solution comprising
  i. one or more film-forming agents;
  ii. a plasticizer in an amount greater than about 1.5% by weight relative to the one or more film-forming agents; and
  iii. optionally, at least one anti-sticking agent, and
  iv. one or more enzyme-friendly organic solvent(s);
cc. coating the pancreatin micropellet cores with the enteric-coating solution wherein the temperature of the pancreatin micropellet cores during coating is kept at a temperature suitable for applying the enteric-coating solution; and
dd. drying the coated pancreatin micropellet cores.

In the foregoing process for producing pancreatin micropellets, the film-forming agent(s), the plasticizer(s), the anti-sticking agent(s) and the enzyme-friendly organic solvents generally have the meanings as previously set forth.

Due to the process for producing pancreatin micropellets, viz. the coating process as described herein, pharmaceutically acceptable residual amounts of the enzyme-friendly organic solvent(s) present in the enteric-coating solution may still be present in the pancreatin micropellet after drying. It is understood that pancreatin micropellets comprising pharmaceutically acceptable residual amounts of enzyme-friendly organic solvent(s) are within the scope of the present invention.

Process step bb) may be performed at a temperature between about 15° C. and about 60° C. Performing process step bb) at ambient temperature (i.e. room temperature, approximately between about 20° C. and about 30° C.), is preferred. Examples of suitable enzyme-friendly organic solvents include acetone, 2-butanol, tert.-butanol, chloroform, dichloromethane, ethanol, methanol, 1-propanol, 2-propanol and mixtures of said solvents. Acetone, ethanol and 2-propanol or their mixtures are preferred as enzyme-friendly organic solvents. Acetone is most preferred. The foregoing list of enzyme-friendly organic solvents in process step bb.) is not meant to be exhaustive but merely illustrative, as a person or ordinary skill in the art would understand that many other enzyme-friendly organic solvents or combination of solvents could also be used.

The enzyme-friendly organic solvent is typically used in an amount between about 6 and about 10 times, preferably between about 7 and about 8 times, the weight of the non-solvent coating constituents used to prepare the pancreatin micropellets. For example, if the non-solvent coating constituents make up to a total weight of about 1.5 g, then about 9 g to about 15 g of enzyme-friendly organic solvent may be used in process step aa).

In process step cc.) the product temperature of the pancreatin micropellet cores, in one embodiment, is usually maintained between about 30° C. and about 60° C. while coating, preferably between about 32° C. and about 55° C., more preferred between about 35° C. and about 50° C., most preferably between about 37° C. and about 49° C. In process step cc.), when cetyl alcohol or a mixture of cetyl alcohol and triethyl citrate is used the product temperature of the pancreatin micropellet cores is maintained between about 40° C. and about 46° C. Maintaining the product temperature of the pancreatin micropellet cores within the preferred temperature ranges while coating results in improved gastric-acid resistant properties of the pancreatin micropellets, in particular when the enteric coating comprise cetyl alcohol and triethyl citrate as plasticizers. The coating in process step cc.) can be accomplished by any process or method known to a person of ordinary skill in the art. Spray coating is preferred. Usually, process step cc.) is performed in a way that the enteric coating comprises between about 20% and about 30% by weight, preferably between about 22% and about 26% by weight and more preferably between about 22.5% and about 25% by weight of the total composition of the pancreatin micropellet. The exact parameters to be applied in process step cc.) to achieve the desired enteric coating will depend on the coating technique used. The person skilled in the art understands how to achieve coating films of a desired thickness when using different coating techniques.

Drying of the enteric-coated pancreatin micropellet cores in process step dd.) is performed between about 30° C. and about 75° C. preferably between about 30° C. and about 55° C., preferably between about 35° C. and about 50° C., and for a period of between about 6 hours and about 60 hours, preferably for a period of between about 10 hours and about 36 hours.

Pancreatin micropellets according to the invention are particularly suitable for delivery of pancreatin and its digestive enzyme constituents to the upper intestine, in particular to the small intestine, usually to the duodenum, of mammals such as humans. Thus, pancreatin micropellets according to the invention are useful for the prophylaxis and/or treatment of various medical conditions and digestive disorders including pancreatic exocrine insufficiency of different origins like maldigestion, and/or for the prophylaxis and/or treatment of pancreatitis, cystic fibrosis, diabetes type I and/or diabetes type II in mammals such as humans. Maldigestion in mammals such as humans is usually based on a deficiency of digestive enzymes, in particular on a deficiency of endogenous lipase, but also of protease and/or amylase. The cause of such a deficiency of digestive enzymes is frequently a hypofunction of the pancreas (e.g. pancreatic insufficiency, usually known as pancreatic exocrine insufficiency), the organ which produces the largest quantity of, and the most important, endogenous digestive enzymes. If the pancreatic insufficiency is pathological, it may be congenital or acquired. Acquired chronic pancreatic insufficiency may, for example, result from alcoholism. Congenital pancreatic insufficiency may, for example, result from disease such as cystic fibrosis. The consequences of the deficiency of digestive enzymes may be severe symptoms of under-nutrition and malnutrition, which may be accompanied by increased susceptibility to secondary illnesses. In one specific embodiment, pancreatin micropellets according to the invention are therefore particularly suited for treating pancreatic exocrine insufficiency of any origin.

In another embodiment, pancreatin micropellets are provided as previously described, for the manufacture of a medicament for the treatment of medical conditions such as digestive disorders, pancreatic exocrine insufficiency, pancreatitis, cystic fibrosis, diabetes type I and/or diabetes type II.

In yet another embodiment, a method is provided for the treatment of a medical condition such as digestive disorders, pancreatic exocrine insufficiency, pancreatitis, cystic fibrosis, diabetes type I and/or diabetes type II by administering a therapeutically effective amount of pancreatin micropellets previously described to a mammalian subject in need of such treatment.

A further embodiment includes a pharmaceutical composition comprising a pharmacologically effective amount of pancreatin wherein the pancreatin is in the form of pancreatin micropellets manufactured according to the processes described herein in a dosage form suitable for oral administration containing said pharmacologically effective amount of pancreatin. The pancreatin micropellets described herein may be placed into pharmaceutically acceptable dosages forms such as capsules or sachets. Capsules or sachets may be opened to permit mixing of the contents with compatible foods or liquids to facilitate administration of the contents of the capsule or sachet.

For proper delivery of an acid-labile drug like pancreatin to the upper intestine of a mammal such as a human, it is necessary that an enteric coating be gastric acid resistant up to a pH of about 5.5. Subsequently, the acid-labile drug will need to be released to the upper intestine which means that the enteric coating must release the acid-labile drug in a less acidic environment, e.g. at about pH 5.5 or higher, in particular at a pH of about 6. The pancreatin micropellets described herein possess superior gastric acid resisting and protective properties, e.g. superior protective properties at about pH 1 and/or about pH 5. Pancreatin micropellets according to the invention wherein the plasticizer is a mixture of cetyl alcohol and triethyl citrate as described above ("CA/TEC-Compositions") are preferred in this regard. Further, CA/TEC-Compositions in general preserve a higher lipase content and usually possess a lower water content relative to other pancreatin micropellets where other plasticizers are used. Furthermore, CA/TEC-Compositions exhibit a favorable dissolution profile which is comparable to the presently marketed pancreatin containing medicaments, e.g. to medicaments available under the trade name Creon™.

In other embodiments of the invention, a pharmaceutical pack or kit is provided comprising one or more containers filled with the pancreatin micropellets described herein. Associated with such container(s) can be various written materials such as instructions for use, or a notice in the form prescribed by a governmental agency regulating the manufacture, use or sale of pharmaceuticals products, which notice reflects approval by the agency of manufacture, use, or sale for human or veterinary administration.

EXAMPLES

The following examples are meant to be illustrative and not to limit the present disclosure. Other suitable modifications and adaptations are of the variety normally encountered by those skilled in the art and are fully within the spirit and scope of the present disclosure.

A. Preparation of Pancreatin Micropellet Cores and Pancreatin Micropellets

1. Preparation of Uncoated Pancreatin Micropellet cores 15.9 kg of pancreatin was mixed with 3.975 kg of polyethylene glycol 4000 in a commercially available high shear mixer and thoroughly moistened with 3.975 kg of 2-propanol. The resulting mixture was extruded by means of a commercially available extruding press which was equipped with a piercing die having 0.8 mm internal diameter bores and a cutting device arranged downstream. The temperature was less than 50° C. while pressing. The extruded mass was cut into extrudate fragments of approximately 5 mm length by means of the cutting device.

The resulting 14.64 kg of the extrudate fragments were transferred in four portions of roughly equal size to a commercially available rounding apparatus and rounded to give approximately elliptically or approximately spherically shaped micropellet cores. An additional 135 g of 2-propanol was added while rounding.

After drying in a commercially available continuous vacuum dryer (Vötsch type) at a temperature in a range from between 35° C. and 50° C. for 12 hours, the pancreatin micropellets were graded, first with a 3.15 mm sieve (sieving of oversize grain >3.15 mm) and then with a 0.7 mm sieve (sieving of undersize grain <0.7 mm) and afterwards with a 1.25 mm sieve (sieving of oversize grain >1.25 mm) to yield 11.98 kg of pancreatin micropellet cores having a pancreatin content of 80% and a bulk density of 0.67 g/ml.

2. Enteric Coating of Pancreatin Micropellet Cores

A coating solution was prepared by adding 1623.2 g of hydroxypropyl methylcellulose phthalate (HP 55), 90.2 g of triethyl citrate, 34.3 g of cetyl alcohol and 38.9 g of dimethicone 1000 to 14030 g of acetone at room temperature while stirring.

5025 g of pancreatin micropellet cores (prepared analogously to the process as described herein) were fed into a commercially available fluid bed coater and were spray-coated at a spray rate of 97-101 kg/h and an air pressure of 1.7 bar with the coating solution as prepared above until the desired film-thickness of the coating had been reached. The product temperature of the pancreatin micropellet cores was monitored and maintained in the range between about 37° C. and about 43° C. during coating. The resulting pancreatin micropellets were then dried in a commercially available vacuum dryer (Vötsch type) at a temperature in a range between 35° C. and 50° C. for 12 hours. The dried pancreatin micropellets were then graded, first with a 0.7 mm sieve (sieving of undersize grain <0.7 mm) and then with a 1.6 mm sieve (sieving of oversize grain >1.6 mm) to yield 6532 g of pancreatin micropellets having a pancreatin content of about 60% relative to the enteric-coated pancreatin micropellets. The bulk density of the pancreatin micropellets was about 0.69 g/ml.

Further pancreatin micropellets were prepared according to the procedure described above and different coatings were applied in a manner similar to the coating process set forth above to yield additional pancreatin micropellets. The compositions of the additional pancreatin micropellets and certain process parameters from the coating processes are given below in Table 1. Composition G can be produced according to processes as described in U.S. Pat. No. 5,378,462. Comparative composition H was prepared according to a process as described above which has been slightly modified (i.e. dibutylphthalate was used as a plasticizer in the coating). All batches have been produced in laboratory scale except where otherwise indicated.

It was an object of the present invention to provide controlled release pharmaceutical compositions for acid-labile drugs, in particular for pancreatin, for delivery of the acid labile drug to the upper intestine which show a good performance and which are substantially free of monomeric phthalic acid ester plasticizers like dibutyl phthalate. The new enteric coating as disclosed herein is substantially free of both, monomeric phthalic acid ester plasticizers, such as dibutyl phthalate, and synthetic oils, such as paraffins or mineral oils, while at the same time providing the desired targeted release and storage stability. The phrase "substantially free of monomeric phthalic acid esters" means that the manufacturing processes described herein and used to make the enteric coating or the enteric coated oral dosage forms of acid-labile drugs where applicable do not utilize one or more monomeric phthalic acid esters (e.g. dibutyl phthalate) as an excipient although monomeric phthalic acid esters may be present as pharmaceutically acceptable trace contaminants in the API, binding agent(s), enteric coating constituents, organic solvents and/or excipients which are used to manufacture the enteric coating and/or the enteric coated oral dosage forms of acid-labile drugs described herein.

TABLE 1

Composition of (enteric-coated) pancreatin micropellets and applicable process parameters

| Ingredients mg/capsule | | A | B | C | D | 1 | 2 |
|---|---|---|---|---|---|---|---|
| Micropellet Cores | Pancreatin | 150.00 | 150.00 | 150.00 | 150.00 | 150.00 | 150.00 |
| | PEG 4000 | 37.50 | 37.50 | 37.50 | 37.50 | 37.50 | 37.50 |
| Enteric Coating (film) | HP 55 | 48.60 | 48.60 | 48.60 | 48.60 | 48.60 | 48.60 |
| | Dimethicone | 1.25 | 1.25 | 1.25 | 1.25 | 1.25 | 1.25 |
| | TEC | 0 | 0 | 3.0 | 4.10 | 5.00 | 0 |
| | CA | 0 | 0.40 | 0 | 0 | 0 | 1.00 |
| | Sum | 237.40 | 237.75 | 240.35 | 241.45 | 242.4 | 238.35 |
| Process parameters | Pellet temp. while coating | 40° C. | 40° C. | 40° C. | 40° C. | 40° C. | 40° C. |

| Ingredients mg/capsule | | 3 | 4 | 5 | 6* | 7 | 8 |
|---|---|---|---|---|---|---|---|
| Micropellet Cores | Pancreatin | 150.00 | 150.00 | 150.00 | 150.00 | 150.00 | 150.00 |
| | PEG 4000 | 37.50 | 37.50 | 37.50 | 37.50 | 37.50 | 37.50 |
| Enteric Coating (film) | HP 55 | 52.60 | 48.60 | 48.60 | 52.25 | 52.25 | 52.25 |
| | Dimethicone | 1.25 | 1.25 | 1.25 | 1.25 | 1.25 | 1.25 |
| | TEC | 0 | 3.60 | 3.00 | 2.90 | 2.90 | 2.90 |
| | CA | 1.15 | 0.40 | 1.00 | 1.10 | 1.10 | 1.10 |
| | Sum | 242.50 | 241.35 | 241.35 | 245.00 | 245.00 | 245.00 |
| Process parameters | Pellet temp. while coating | 40° C. | 40° C. | 40° C. | 40° C. | 30° C. | 35° C. |

| Ingredients mg/capsule | | 9 | 10 | 11 | 12 | 13 | 14 |
|---|---|---|---|---|---|---|---|
| Micropellet Cores | Pancreatin | 150.00 | 150.00 | 150.00 | 150.00 | 150.00 | 150.00 |
| | PEG 4000 | 37.50 | 37.50 | 37.50 | 37.50 | 37.50 | 37.50 |
| Enteric Coating (film) | HP 55 | 56.34 | 56.34 | 56.34 | 52.25 | 52.25 | 56.34 |
| | Dimethicone | 1.35 | 1.35 | 1.35 | 1.25 | 1.25 | 1.35 |
| | TEC | 3.13 | 3.13 | 3.13 | 2.90 | 2.90 | 3.13 |
| | CA | 1.19 | 1.19 | 1.19 | 1.10 | 1.10 | 1.19 |
| | Sum | 249.51 | 249.51 | 249.51 | 245.00 | 245.00 | 249.51 |
| Process parameters | Pellet temp. while coating | 37° C. | 40° C. | 43° C. | 49° C. | 40° C. | 46° C. |

| Ingredients mg/capsule | | 15 | E | F | G | H |
|---|---|---|---|---|---|---|
| Micropellet Cores | Pancreatin | 128.06 | 150.00 | 150.00 | 150.00 | 150.00 |
| | PEG 4000 | 32.01 | 37.50 | 37.50 | 37.50 | 37.50 |
| | Light mineral oil | 0 | 0 | 0 | 3.75 | 0 |

TABLE 1-continued

Composition of (enteric-coated) pancreatin micropellets and applicable process parameters

| | | | | | | |
|---|---|---|---|---|---|---|
| Enteric Coating (film) | HP 55 | 48.10 | 48.60 | 48.60 | 48.60 | 48.60 |
| | Dimethicone | 1.15 | 1.25 | 1.25 | 1.25 | 1.25 |
| | TEC | 2.67 | 1.00 | 2.00 | 0 | 0 |
| | CA | 1.01 | 0 | 0 | 0 | 0 |
| | DBP | 0 | 0 | 0 | 4.10 | 4.10 |
| | Light mineral oil | 0 | 0 | 0 | 3.30 | 0 |
| | Sum | 213.00 | 238.35 | 239.35 | 248.50 | 241.50 |
| Process parameters | Pellet temp. while coating | n.a. | 40° C. | 40° C. | 40° C. | 40° C. |

PEG = polyethylene glycol; TEC = triethyl citrate; CA = cetyl alcohol; HP 55 = hydroxypropyl methylcellulose phthalate; temp. = temperature; DBP = dibutyl phthalate; * = production scale; n.a.: data not available.

Composition G is a currently available high-quality pharmaceutical composition comprising pancreatin and light mineral oil.

Compositions No. 6, 10, 13, 14 and 15 are examples of CA/TEC compositions.

Composition No. 3 is an example of a composition comprising cetyl alcohol as the plasticizer.

B. Determination of the Gastric Acid Resistance of Enteric-Coated Pancreatin Micropellets at pH 1 and pH 5

The gastric acid resistances of the pancreatin micropellets (see Table 1 hereabove) were measured.

Resistance to gastric juice (pH 1) of the different pancreatin micropellets from Table 1 was determined by immersing the pancrelipase micropellets for 2 hours in 0.1 mol/l hydrochloric acid in a disintegration tester according to the European Pharmacopoeia (Ph. Eur.). Then the un-dissolved portion of the pellets was separated from the solution and their residual lipase activity was determined according to the lipase assay of Ph. Eur./The International Pharmaceutical Federation" (FIP), PO Box 84200; 2508 AE The Hague; The Neterlands. The results of these tests for gastric resistance of the enteric coating are presented in Table 2 ("stability at pH 1").

Further, a similar test at pH 5 was performed using the same conditions as outlined above, with the exception that a phosphate buffer pH 5.0 (2.0 g sodium chloride and 9.2 g sodium di-hydrogen phosphate monohydrate per liter adjusted to pH 5.0) was used as a solvent instead of 0.1 mol/l hydrochloric acid. The results of these tests for gastric resistance are also presented below in Table 2 ("stability at pH 5").

The gastric acid resistances of the compositions from Table 1 (see above) are each given in Table 2 as percentages of the residual lipolytic activity after the incubation in relation to the actual lipolytic activity of the samples tested prior to the incubation (relative gastric acid resistance). The lipolytic activity is determined according to the lipase assay described in the USP monograph "pancrelipase delayed-release capsules". In principle, any standardized and characterized pancreatin sample may be used as the lipase reference standard. For example, a predetermined lipolytic activity standard may be obtained from the "International Pharmaceutical Federation" (FIP), PO Box 84200; 2508 AE The Hague; The Netherlands. For the purposes of the present invention, an internal pancreatin standard was used which is available on request from Solvay Pharmaceuticals GmbH, Hans-Boeckler-Allee 20, 30173 Hannover, Germany.

TABLE 2

Relative gastric acid resistances (stabilities) of the pancreatin micropellets at pH 1 and pH 5

| Composition | Stability at pH 5 [%] | Stability at pH 1 [%] |
|---|---|---|
| A | 15.3 | 15.9 |
| B | 63.2 | 53.8 |
| C | 71.6 | 84.2 |
| D | 52.0 | 93.6 |
| 1 | 87.0 | 96.0 |
| 2 | 76.4 | 92.6 |
| 3 | 92.1 | 94.5 |
| 4 | 85.3 | 93.7 |
| 5 | 92.0 | 93.0 |
| 6 | 94.9 | 99.4 |
| 7 | 67.4 | 89.8 |
| 8 | 80.5 | 95.2 |
| 9 | 83.8 | 90.8 |
| 10 | 97.9 | 99.6 |
| 11 | 89.0 | 93.5 |
| 12 | 83.7 | 94.8 |
| 13 | 100.2 | 102.7 |
| 14 | 93.6 | 98.7 |
| E | 48.6 | 65.0 |
| F | 36.5 | 75.0 |
| G | 98.6 | 100.6 |

Preferred pancreatin micropellets have a gastric acid resistance (stability) at pH 1 of at least 75%, in particular of at least 85%, preferably of at least 90%, more preferred of at least 95%, relative to a predetermined pancreatin lipolytic activity standard.

Other preferred pancreatin micropellets as disclosed herein have a gastric acid resistance at pH 5 of at least 75%, in particular of at least 85%, preferably of at least 90%, more preferred of at least 95%, relative to a predetermined pancreatin lipolytic activity standard.

Pancreatin micropellets which are most preferred have a gastric acid resistance at pH 1 of at least 90% and an additional gastric acid resistance at pH 5 of at least 90%, relative to a predetermined pancreatin lipolytic activity standard.

C. Determination of the Dissolution Profile of Enteric Coated Pancreatin Microrellets The dissolution profile of different enteric coated pancreatin micropellets from Table 1 (see above) was determined according to a test procedure as described in the United States Pharmacopoeia (USP) monograph "pancrelipase delayed-release capsules" with increased gastric resistance phase which is hereby incorporated by reference.

The determination of the resistance to gastric fluid was performed using gastric juice without enzymes according to USP under standardized conditions (37° C., 100 rpm) for 2 hours in the dissolution apparatus (basket apparatus USP). Then the un-dissolved portion of the enteric coated pancreatin micropellets was separated from the solution and transferred into the paddle apparatus according to USP, filled with phosphate buffer solution at pH 6.0 to determine the dissolution of enzymes. The enteric coated pancreatin micropellets were agitated in a dissolution tester under standardized conditions for usually 90 minutes (see exact timepoints in Table 3 below) at 37° C. and 50 rpm.

The lipase activity was determined after selected time points (see Table 3) according to the lipase assay described in the USP monograph "pancrelipase delayed-release capsules".

The results of the dissolution profile test are presented as "% residual lipase activity of actual lipase activity" below (see Table 3).

TABLE 3

Dissolution profiles of the enteric coated pancreatin micropellets in phosphate buffer

| Time points | % lipase activity of initial actual activity for pancreatin micro-pellet composition No. | | | | | |
|---|---|---|---|---|---|---|
| [min.] | G | H | 3 | 5 | 13 | 14 |
| 5 | 0.0 | 4 | 3.0 | 0.0 | 4.6 | NA |
| 10 | 0.0 | 6.25 | 4.9 | 6.2 | 4.6 | 15.37 |
| 15 | 11.9 | 23.15 | 16.4 | 37.8 | 17.6 | 34.38 |
| 20 | 48.0 | 48.15 | 39.3 | 63.5 | 40.8 | NA |
| 25 | 62.3 | 62.9 | 59.0 | 72.4 | 59.8 | NA |
| 30 | 73.5 | 69.6 | 67.8 | 80.0 | 66.2 | 73.86 |
| 45 | 77.1 | 77.15 | 80.5 | 84.0 | 76.6 | 84.45 |
| 60 | 79.9 | 78.35 | 77.8 | 84.2 | 81.9 | 81.25 |
| 75 | 78.4 | 76.7 | 77.1 | 78.9 | 79.8 | 80.40 |
| 90 | 78.2 | 75.25 | 72.3 | 77.2 | 77.4 | NA |

For the dissolution profile test results as provided in Table 3, a comparison of the compositions G, H and 14 was performed. The comparison was based on the "Guidance for Industry", SUPAC-MR, Modified Release Solid Oral Dosage Forms (September 1997) by calculating the similarity factor (f2). The 2 acceptance limits for determining similarity of two compared curves were (i) a factor (f2) >50 and (ii) the average deviation at any dissolution sampling point should not be greater than 15%.

In vitro dissolution profile comparisons can be made using a model independent approach using similarity factor. Dissolution profiles may be compared using the following equation that defines a similarity factor ($f_2$):

$$f_2 = 50 \log\{[1 + 1/n\Sigma_{t=1}^{n}(R_t - T_t)^2]^{-0.5} * 100\}$$

where log=logarithm to base 10, n=number of sampling time points, Σ=summation over all time points, $R_t$=dissolution at time point t of the reference (unchanged drug product, i.e., prechange batch), $T_t$=dissolution at time point t of the test (changed drug product, i.e., post-change batch).

One embodiment includes a composition comprising enteric coated pancreatin micropellets wherein the percent lipase activity present in a phosphate buffer solution is greater than 0% after 10 minutes, greater than about 30% after 20 minutes, greater than about 50% after 30 minutes and greater than about 65% after 60 minutes as measured according to the United States Pharmacopoeia using a phosphate buffer solution at pH 6 wherein pancreatin micropellets are substantially free of synthetic oils.

When applying the above-stated acceptance limits for determining similarity it was found that the dissolution profiles of pancreatin micropellet compositions no. 3 and 13 (see Table 1) could be considered to be similar to the dissolution profile of the reference pancreatin micropellet "G" (see Table 1). Thus, pharmaceutical compositions containing pancreatin and their methods of manufacturing which are similar to composition G in Table 1 are specifically described herein.

D. Storage Stability Studies for Enteric Coated Pancreatin Micropellet Controlled Release Pharmaceutical Compositions (CRPCs)

For determining storage stability of different pancreatin micropellets from Table 1 (see above), hard gelatin capsules of size 0 were filled with approximately 497 mg of pancreatin micropellets (see Table 1) and packed into 30 ml HDPE bottles for performing the following tests.

The packed pancreatin micropellets were stored for 5 months under normal or two different aggravated storage conditions (see below for details) and the residual lipase activity was determined in each case analogously to the instructions of Ph. Eur. The results of these storage stability tests of the CRPCs after 5 months' storage periods are presented below in Tables 4a and 4b, respectively ("Lipase").

Resistance to gastric juice (pH 1) of the different pancreatin micropellets from Table 1 was also determined after a total storage period of 5 months by immersing pancrelipase delayed-release pellets for 2 hours in 0.1 mol/l hydrochloric acid in a disintegration tester according to the Ph. Eur. (Section 2.9.1. "disintegration"). The un-dissolved portion of the pellets was then separated from the solution and their residual lipase activity was determined according to the lipase assay of Ph. Eur. (monograph "pancreas powder"). The results of these tests for gastric resistance of the enteric coating after 5 months' storage periods under normal or two different aggravated storage conditions are presented in Tables 4a and 4b, respectively ("gastric resistance at pH 1").

Further, a similar test at pH 5 was done using the same conditions as outlined in the previous paragraph, with the exception that a phosphate buffer pH 5.0 (2.0 g sodium chloride and 9.2 g sodium di-hydrogen phosphate monohydrate per liter adjusted to pH 5.0) was used as a solvent instead of 0.1 mol/l hydrochloric acid. The results of these tests for gastric resistance of the enteric coating after 5 months' storage periods are presented below in Tables 4a and 4b, respectively ("gastric resistance at pH 5").

TABLE 4a

Stability results for select compositions from Table 1 at 30° C. and 65% rel. humidity (slightly aggravated storage conditions)

| | | % lipase activity of initial activity Months | |
|---|---|---|---|
| Conditions | CRPC No. | 0 | 5 |
| Lipase (initial activity) | G | 100 | 92 |
| | 3 | 100 | 88 |
| | 13 | 100 | 94 |
| Gastric resistance at pH 1 (actual activity) | G | 101 | 91 |
| | 3 | 95 | 95 |
| | 13 | 103 | 99 |
| Gastric resistance at pH 5 (actual activity) | G | 99 | 92 |
| | 3 | 92 | 86 |
| | 13 | 100 | 95 |

TABLE 4b

Stability results for select compositions from Table 1 at 40° C. and 75% rel. humidity (aggravated storage conditions)

| | | % lipase activity of initial activity Months | | | | | |
|---|---|---|---|---|---|---|---|
| Conditions | CRPC No. | 0 | 1 | 2 | 3 | 4 | 5 |
| Lipase (initial activity) | G | 100 | 90 | 80 | 77 | 69 | 64 |
| | 3 | 100 | 87 | 79 | 69 | 64 | 61 |
| | 13 | 100 | 97 | 87 | 81 | 73 | 67 |
| Gastric resistance a pH | G | 101 | 96 | 101 | 94 | 96 | 96 |
| | 3 | 95 | 94 | 94 | 96 | 87 | 86 |

TABLE 4b-continued

Stability results for select compositions from Table 1 at 40° C. and 75% rel. humidity (aggravated storage conditions)

| Conditions | CRPC No. | % lipase activity of initial activity Months | | | | | |
|---|---|---|---|---|---|---|---|
| | | 0 | 1 | 2 | 3 | 4 | 5 |
| 1 (actual activity) | 13 | 103 | 95 | 97 | 97 | 96 | 89 |
| Gastric | G | 99 | 92 | 95 | 76 | 87 | 40 |
| resistance at pH | 3 | 92 | 86 | 78 | 63 | 51 | 22 |
| 5 (actual activity) | 13 | 100 | 90 | 83 | 73 | 43 | 15 |

The data presented in Tables 4a and 4b illustrate that the tested composition Nos. G, 3 and 13 (see Table 1) are of satisfactory storage stability under normal and slightly aggravated storage conditions over a 5 months storage period. The lipase content of composition No. 13, although similar to the two comparative compositions, was best preserved over the observed 5 months' periods under slightly aggravated and aggravated storage conditions.

Under slightly aggravated storage conditions, which are most relevant in practice, composition No. 13 performed best in terms of gastric resistance at pH 1 and pH 5 over the observed 5 months' periods.

All references, including publications, patent applications, and patents, cited herein are hereby incorporated by reference to the same extent as if each reference there individually and specifically indicated to be incorporated by reference were set forth in its entirety herein.

The use of the terms "a" and "an" and "the" and similar references in the context of this disclosure (especially in the context of the following claims) are to be construed to cover both the singular and the plural, unless otherwise indicated herein or clearly contradicted by context. All methods described herein can be performed in any suitable order unless otherwise indicated herein or otherwise clearly contradicted by context. The use of any and all examples, or exemplary language (e.g., such as, preferred, preferably) provided herein, is intended merely to further illustrate the content of the disclosure and does not pose a limitation on the scope of the claims. No language in the specification should be construed as indicating any non-claimed element as essential to the practice of the invention.

Alternative embodiments of the claimed invention are described herein, including the best mode known to the inventors for carrying out the claimed invention. Of these, variations of the disclosed embodiments will become apparent to those of ordinary skill in the art upon reading the foregoing disclosure. The inventors expect skilled artisans to employ such variations as appropriate, and the inventors intend for the invention to be practiced otherwise than as specifically described herein.

Accordingly, this invention includes all modifications and equivalents of the subject matter recited in the claims appended hereto as permitted by applicable law. Moreover, any combination of the above described elements in all possible variations thereof is encompassed by the invention unless otherwise indicated herein or otherwise clearly contradicted by context.

The use of individual numerical values are stated as approximations as though the values were preceded by the word "about" or "approximately" unless clearly indicated otherwise by context. Similarly, the numerical values in the various ranges specified in this application, unless expressly indicated otherwise, are stated as approximations as though the minimum and maximum values within the stated ranges were both preceded by the word "about" or "approximately." In this manner, variations above and below the stated ranges can be used to achieve substantially the same results as values within the ranges. As used herein, the terms "about" and "approximately" when referring to a numerical value shall have their plain and ordinary meanings to a person of ordinary skill in the art to which the claimed subject matter is most closely related or the art relevant to the range or element at issue. The amount of broadening from the strict numerical boundary depends upon many factors. For example, some of the factors which may be considered include the criticality of the element and/or the effect a given amount of variation will have on the performance of the claimed subject matter, as well as other considerations known to those of skill in the art. As used herein, the use of differing amounts of significant digits for different numerical values is not meant to limit how the use of the words "about" or "approximately" will serve to broaden a particular numerical value. Thus, as a general matter, "about" or "approximately" broaden the numerical value. Also, the disclosure of ranges is intended as a continuous range including every value between the minimum and maximum values plus the broadening of the range afforded by the use of the term "about" or "approximately". Thus, recitation of ranges of values herein are merely intended to serve as a shorthand method of referring individually to each separate value falling within the range, unless otherwise indicated herein, and each separate value is incorporated into the specification as if it were individually recited herein.

We claim:

1. A process for the manufacture of enteric-coated pancreatin micropellets, comprising the steps of:
   a. preparing an extrudable mixture consisting of:
      i. pancreatin;
      ii. at least one pharmaceutically acceptable binding agent, wherein the binding agent is selected from the group consisting of: polyethylene glycol 2000, polyethylene glycol 3000, polyethylene glycol 4000, polyethylene glycol 6000, polyethylene glycol 8000 and polyethylene glycol 10000; and
      iii. one or more enzyme-friendly organic solvents in an amount sufficient to form an extrudable mixture;
   b. creating pancreatin micropellet cores from the extrudable mixture by extrusion;
   c. forming the uncoated pancreatin micropellet cores into approximately spherical or approximately ellipsoidal shape, wherein step (c) consists of rounding, in a spheronizer, the uncoated pancreatin micropellet cores in the presence of additional enzyme-friendly organic solvent;
   d. removing the one or more enzyme-friendly organic solvents from the pancreatin micropellet cores such that the pancreatin micropellet cores are substantially free of the one or more enzyme-friendly organic solvents; and
   e. coating the pancreatin micropellet cores with an enteric coating;
   wherein the pancreatin micropellet cores are substantially free of synthetic oils in each of steps (b), (c), and (d).

2. The process of claim 1 wherein the pharmaceutically acceptable binding agent is polyethylene glycol 4000.

3. The process of claim 2 wherein the pancreatin is present between 70% and 90% weight to weight of the uncoated pancreatin micropellet cores.

4. The process of claim 2 wherein polyethylene glycol 4000 is present between 10% and 30% weight to weight of the uncoated pancreatin micropellet cores.

5. The process of claim 1 wherein the one or more enzyme-friendly organic solvents is selected from the group consisting of: acetone, chloroform, dichloromethane, methanol, ethanol, 1-propanol, 2-propanol, 2-butanol, tert-butanol and mixtures of said solvents.

6. The process of claim 1 wherein the pancreatin is present at 80% weight to weight of the uncoated pancreatin micropellet cores.

7. A pharmaceutical composition comprising an enteric-coated pancreatin micropellet manufactured according to the process of claim 1.

8. The pharmaceutical composition of claim 7, wherein the enteric-coated pancreatin micropellet comprises:
   (a) a pancreatin micropellet core, wherein the core consists of:
      (i) 70% to 90% pancreatin; and
      (ii) 10% to 30% of the pharmaceutically acceptable binding agent; and
   (b) the enteric coating;
   wherein the percentages of components in the pancreatin micropellet core are weight to weight of the uncoated pancreatin micropellet core.

9. The pharmaceutical composition of claim 7, wherein the enteric-coated micropellet is substantially free of synthetic oils.

10. The pharmaceutical composition of claim 8, wherein at least of 55% of lipase activity in the composition is released within 30 minutes in a buffer solution at pH 6 as measured according to United States Pharmacopoeia.

11. A delayed-release oral pharmaceutical composition comprising:
   (a) a pancreatin core, wherein the core consists of:
      (i) 65% to 90% pancreatin;
      (ii) 5% to 30% of at least one pharmaceutically acceptable binding agent;
      (iii) optionally, at least one pharmaceutically acceptable excipient, wherein synthetic oils are not pharmaceutically acceptable excipients; and
      (iv) an enzyme-friendly organic solvent, wherein synthetic oils are not enzyme-friendly organic solvents, wherein the percentages of components are weight to weight of the core; and
   (b) an enteric coating on the core;
   wherein at least 55% of lipase activity in the composition is released within 30 minutes in a buffer solution at pH 6 as measured according to United States Pharmacopoeia.

12. The pharmaceutical composition of claim 11, wherein the composition has a relative gastric acid resistance of 75% or more following incubation for 2 hours in 0.1 mol/l hydrochloric acid at pH 1.

13. The pharmaceutical composition of claim 11, wherein the composition has a relative gastric acid resistance of 75% or more following incubation for 2 hours in a phosphate buffer solution at pH 5.

14. The pharmaceutical composition of claim 11, wherein the pancreatin cores are in the form of micropellets.

15. The pharmaceutical composition of claim 14, wherein the micropellets have a diameter of about 0.5 mm to about 2.0 mm.

16. A delayed-release oral pharmaceutical composition comprising:
   (a) pancreatin micropellet cores comprising
      (i) pancreatin;
      (ii) at least one pharmaceutically acceptable binding agent, wherein synthetic oils are not pharmaceutically acceptable binding agents; and
      (iii) an enzyme-friendly organic solvent, wherein synthetic oils are not enzyme-friendly organic solvents; and
   (b) an enteric coating on the cores;
   wherein the enteric coating is substantially free of monomeric phthalic acid esters;
   wherein the composition has a relative gastric acid resistance of 75% or more following incubation for 2 hours in a phosphate buffer solution at pH 5; and
   wherein at least 65% of lipase activity in the enteric coated pancreatin micropellets is released in 30 minutes in a phosphate buffer solution at pH 6.0 at 37° C., in a dissolution apparatus, using a paddle speed of 50 rpm, following 2 hours incubation in a gastric juice without enzymes at 37° C., in a dissolution apparatus, using a speed of 100 rpm.

17. The pharmaceutical composition of claim 16, wherein greater than 0% of lipase activity in the enteric coated pancreatin micropellets is released within 10 minutes in a phosphate buffer solution at pH 6 at 37° C., in a dissolution apparatus, using a paddle speed of 50 rpm, following 2 hours incubation in a gastric juice without enzymes at 37° C., in a dissolution apparatus, using a speed of 100 rpm.

18. The pharmaceutical composition of claim 16, wherein greater than 15% of lipase activity in the enteric coated pancreatin micropellets is released within 15 minutes, greater than 65% of lipase activity in the enteric coated pancreatin micropellets is released within 30 minutes, and greater than 75% of lipase activity in the composition enteric coated pancreatin micropellets is released within 45 minutes, in a phosphate buffer solution at pH 6 at 37° C., in a dissolution apparatus, using a paddle speed of 50 rpm, following 2 hours incubation in a gastric juice without enzymes at 37° C., in a dissolution apparatus, using a speed of 100 rpm.

19. The pharmaceutical composition of claim 16, wherein the at least one pharmaceutically acceptable binding agent is selected from the group consisting of: polyethylene glycol 2000, polyethylene glycol 3000, polyethylene glycol 4000, polyethylene glycol 6000, polyethylene glycol 8000 and polyethylene glycol 10000.

20. The pharmaceutical composition of claim 19, wherein the at least one pharmaceutically acceptable binding agent is polyethylene glycol 4000.

21. The pharmaceutical composition of claim 16, wherein the pancreatin micropellet cores consist essentially of 70% to 90% pancreatin by weight of the core.

22. The pharmaceutical composition of claim 16, wherein the pancreatin micropellet cores consist essentially of 10% to 30% of the at least one pharmaceutically acceptable binding agent by weight of the core.

23. The pharmaceutical composition of claim 22, wherein the at least one pharmaceutically acceptable binding agent is selected from the group consisting of: polyethylene glycol 2000, polyethylene glycol 3000, polyethylene glycol 4000, polyethylene glycol 6000, polyethylene glycol 8000 and polyethylene glycol 10000.

24. The pharmaceutical composition of claim 23, wherein the at least one pharmaceutically acceptable binding agent is polyethylene glycol 4000.

25. The pharmaceutical composition of claim 16, wherein the micropellet cores have a diameter of less than 5 mm.

26. The pharmaceutical composition of claim 16, wherein the micropellet cores have a diameter of about 0.5 mm to about 2.0 mm.

27. The pharmaceutical composition of claim 16, wherein the enteric coating comprises hydroxypropyl cellulose, hydroxypropylmethyl acetate succinate, hydroxypropyl methyl cellulose acetate succinate, hydroxypropyl methylcellulose phthalate or methyl cellulose.

28. The pharmaceutical composition of claim 16, wherein the enteric coating comprises hydroxypropyl methyl cellulose acetate succinate or hydroxypropyl methylcellulose phthalate.

29. The pharmaceutical composition of claim 26, wherein the enteric coating comprises hydroxypropyl methyl cellulose acetate succinate or hydroxypropyl methylcellulose phthalate.

30. The pharmaceutical composition of claim 16, wherein the composition has a relative gastric acid resistance of 75% or more following incubation for 2 hours in 0.1 mol/l hydrochloric acid at pH 1.

31. The pharmaceutical composition of claim 28, wherein the composition has a relative gastric acid resistance of 75% or more following incubation for 2 hours in 0.1 mol/l hydrochloric acid at pH 1.

32. The pharmaceutical composition of claim 16, wherein the composition has a relative gastric acid resistance of 90% or more following incubation for 2 hours in a phosphate buffer at pH 5.

33. The pharmaceutical composition of claim 28, wherein the composition has a relative gastric acid resistance of 90% or more following incubation for 2 hours in a phosphate buffer at pH 5.

34. The pharmaceutical composition of claim 16, wherein the micropellet cores contain less than 3% water.

35. The pharmaceutical composition of claim 19, wherein the micropellet cores contain less than 3% water.

36. The pharmaceutical composition of claim 21, wherein the micropellet cores contain less than 3% water.

37. The pharmaceutical composition of claim 14, wherein the micropellets have a diameter of less than 5 mm.

38. The pharmaceutical composition of claim 15, wherein the at least one pharmaceutically acceptable binding agent is polyethylene glycol 4000.

39. The pharmaceutical composition of claim 16, wherein the pancreatin micropellet cores consist essentially of 70% to 90% pancreatin by weight of the core; the at least one pharmaceutically acceptable binding agent is polyethylene glycol 4000; and the micropellet cores have a diameter of about 0.5 mm to about 2.0 mm.

40. The pharmaceutical composition of claim 16, wherein the dissolution of the enteric coated pancreatin micropellets is determined according to United States Pharmacopoeia monograph for pancrelipase delayed-release capsules.

41. The pharmaceutical composition of claim 11, wherein the at least one pharmaceutically acceptable binding agent is polyethylene glycol 4000.

42. The pharmaceutical composition of claim 11, wherein the enteric coating is substantially free of monomeric phthalic acid esters.

43. The pharmaceutical composition of claim 11, wherein at least 65% of lipase activity in the enteric coated pancreatin micropellets is released in 30 minutes in a phosphate buffer solution at pH 6.0 at 37° C., in a dissolution apparatus, using a paddle speed of 50 rpm, following 2 hours incubation in a gastric juice without enzymes at 37° C., in a dissolution apparatus, using a speed of 100 rpm.

44. The pharmaceutical composition of claim 11, wherein at least 65% of lipase activity in the enteric coated pancreatin micropellets is released in 30 minutes when the dissolution of the enteric coated pancreatin micropellets is determined according to United States Pharmacopoeia monograph for pancrelipase delayed-release capsules.

45. A delayed-release oral pharmaceutical composition comprising:
(a) pancreatin micropellet cores comprising
(i) one active pharmaceutical ingredient consisting essentially of pancreatin,
(ii) at least one pharmaceutically acceptable binding agent, wherein synthetic oils are not pharmaceutically acceptable binding agents, and
(iii) an enzyme-friendly organic solvent, wherein synthetic oils are not enzyme-friendly organic solvents,
wherein the cores contain less than 2% synthetic oils; and
(b) an enteric coating on the cores, wherein the enteric coating is substantially free of monomeric phthalic acid esters;
wherein the composition has a relative gastric acid resistance of 75% or more following incubation for 2 hours in a phosphate buffer solution at pH 5; and
wherein at least 65% of lipase activity in the enteric coated pancreatin micropellets is released in 30 minutes in a phosphate buffer solution at pH 6.0 at 37° C., in a dissolution apparatus, using a paddle speed of 50 rpm, following 2 hours incubation in a gastric juice without enzymes at 37° C., in a dissolution apparatus, using a speed of 100 rpm.

46. The pharmaceutical composition of claim 45, wherein greater than 0% of lipase activity in the enteric coated pancreatin micropellets is released within 10 minutes in a phosphate buffer solution at pH 6 at 37° C., in a dissolution apparatus, using a paddle speed of 50 rpm, following 2 hours incubation in a gastric juice without enzymes at 37° C., in a dissolution apparatus, using a speed of 100 rpm.

47. The pharmaceutical composition of claim 45, wherein greater than 15% of lipase activity in the enteric coated pancreatin micropellets is released within 15 minutes, greater than 65% of lipase activity in the enteric coated pancreatin micropellets is released within 30 minutes, and greater than 75% of lipase activity in the enteric coated pancreatin micropellets is released within 45 minutes, in a phosphate buffer solution at pH 6 at 37° C., in a dissolution apparatus, using a paddle speed of 50 rpm, following 2 hours incubation in a gastric juice without enzymes at 37° C., in a dissolution apparatus, using a speed of 100 rpm.

48. The pharmaceutical composition of claim 45, wherein the at least one pharmaceutically acceptable binding agent is selected from the group consisting of: polyethylene glycol 2000, polyethylene glycol 3000, polyethylene glycol 4000, polyethylene glycol 6000, polyethylene glycol 8000 and polyethylene glycol 10000.

49. The pharmaceutical composition of claim 48, wherein the at least one pharmaceutically acceptable binding agent is polyethylene glycol 4000.

50. The pharmaceutical composition of claim 45, wherein the pancreatin micropellet cores consist essentially of 70% to 90% pancreatin by weight of the core.

51. The pharmaceutical composition of claim 45, wherein the pancreatin micropellet cores consist essentially of 10% to 30% of the at least one pharmaceutically acceptable binding agent by weight of the core.

52. The pharmaceutical composition of claim 51, wherein the at least one pharmaceutically acceptable binding agent is selected from the group consisting of: polyethylene glycol 2000, polyethylene glycol 3000, polyethylene glycol 4000, polyethylene glycol 6000, polyethylene glycol 8000 and polyethylene glycol 10000.

53. The pharmaceutical composition of claim 52, wherein the at least one pharmaceutically acceptable binding agent is polyethylene glycol 4000.

54. The pharmaceutical composition of claim 45, wherein the micropellet cores have a diameter of less than 5 mm.

55. The pharmaceutical composition of claim 45, wherein the micropellet cores have a diameter of about 0.5 mm to about 2.0 mm.

56. The pharmaceutical composition of claim 45, wherein the enteric coating comprises hydroxypropyl cellulose, hydroxypropylmethyl acetate succinate, hydroxypropyl methyl cellulose acetate succinate, hydroxypropyl methylcellulose phthalate or methyl cellulose.

57. The pharmaceutical composition of claim 45, wherein the enteric coating comprises hydroxypropyl methyl cellulose acetate succinate or hydroxypropyl methylcellulose phthalate.

58. The pharmaceutical composition of claim 55, wherein the enteric coating comprises hydroxypropyl methyl cellulose acetate succinate or hydroxypropyl methylcellulose phthalate.

59. The pharmaceutical composition of claim 45, wherein the composition has a relative gastric acid resistance of 75% or more following incubation for 2 hours in 0.1 mol/l hydrochloric acid at pH 1.

60. The pharmaceutical composition of claim 57, wherein the composition has a relative gastric acid resistance of 75% or more following incubation for 2 hours in 0.1 mol/l hydrochloric acid at pH 1.

61. The pharmaceutical composition of claim 45, wherein the composition has a relative gastric acid resistance of 90% or more following incubation for 2 hours in a phosphate buffer at pH 5.

62. The pharmaceutical composition of claim 57, wherein the composition has a relative gastric acid resistance of 90% or more following incubation for 2 hours in a phosphate buffer at pH 5.

63. The pharmaceutical composition of claim 45, wherein the micropellet cores contain less than 3% water.

64. The pharmaceutical composition of claim 48, wherein the micropellet cores contain less than 3% water.

65. The pharmaceutical composition of claim 50, wherein the micropellet cores contain less than 3% water.

66. The pharmaceutical composition of claim 45, wherein the pancreatin micropellet cores consist essentially of 70% to 90% pancreatin by weight of the core; the at least one pharmaceutically acceptable binding agent is polyethylene glycol 4000; and the micropellet cores have a diameter of about 0.5 mm to about 2.0 mm.

67. The pharmaceutical composition of claim 45, wherein the dissolution of the enteric coated pancreatin micropellets is determined according to United States Pharmacopoeia monograph for pancrelipase delayed-release capsules.

68. A delayed-release oral pharmaceutical composition comprising:
  (a) pancreatin micropellet cores consisting essentially of pancreatin and one or more suitable pharmaceutically acceptable excipients, wherein at least one excipient is a pharmaceutically acceptable binding agent, and an enzyme-friendly organic solvent, wherein synthetic oils are not pharmaceutically acceptable binding agents and wherein synthetic oils are not enzyme-friendly organic solvents; and
  (b) an enteric coating on the cores, wherein the enteric coating is substantially free of monomeric phthalic acid esters;
  wherein the composition has a relative gastric acid resistance of 75% or more following incubation for 2 hours in a phosphate buffer solution at pH 5; and wherein at least 65% of lipase activity in the enteric coated pancreatin micropellets is released in 30 minutes in a phosphate buffer solution at pH 6.0 at 37° C., in a dissolution apparatus, using a paddle speed of 50 rpm, following 2 hours incubation in a gastric juice without enzymes at 37° C., in a dissolution apparatus, using a speed of 100 rpm.

69. The pharmaceutical composition of claim 68, wherein greater than 0% of lipase activity in the enteric coated pancreatin micropellets is released within 10 minutes in a phosphate buffer solution at pH 6 at 37° C., in a dissolution apparatus, using a paddle speed of 50 rpm, following 2 hours incubation in a gastric juice without enzymes at 37° C., in a dissolution apparatus, using a speed of 100 rpm.

70. The pharmaceutical composition of claim 68, wherein greater than 15% of lipase activity in the enteric coated pancreatin micropellets is released within 15 minutes, greater than 65% of lipase activity in the enteric coated pancreatin micropellets is released within 30 minutes, and greater than 75% of lipase activity in the enteric coated pancreatin micropellets is released within 45 minutes, in a phosphate buffer solution at pH 6 at 37° C., in a dissolution apparatus, using a paddle speed of 50 rpm, following 2 hours incubation in a gastric juice without enzymes at 37° C., in a dissolution apparatus, using a speed of 100 rpm.

71. The pharmaceutical composition of claim 68, wherein the at least one pharmaceutically acceptable binding agent is selected from the group consisting of: polyethylene glycol 2000, polyethylene glycol 3000, polyethylene glycol 4000, polyethylene glycol 6000, polyethylene glycol 8000 and polyethylene glycol 10000.

72. The pharmaceutical composition of claim 71, wherein the at least one pharmaceutically acceptable binding agent is polyethylene glycol 4000.

73. The pharmaceutical composition of claim 68, wherein the pancreatin micropellet cores consist essentially of 70% to 90% pancreatin by weight of the core.

74. The pharmaceutical composition of claim 68, wherein the pancreatin micropellet cores consist essentially of 10% to 30% of the at least one pharmaceutically acceptable binding agent by weight of the core.

75. The pharmaceutical composition of claim 74, wherein the at least one pharmaceutically acceptable binding agent is selected from the group consisting of: polyethylene glycol 2000, polyethylene glycol 3000, polyethylene glycol 4000, polyethylene glycol 6000, polyethylene glycol 8000 and polyethylene glycol 10000.

76. The pharmaceutical composition of claim 75, wherein the at least one pharmaceutically acceptable binding agent is polyethylene glycol 4000.

77. The pharmaceutical composition of claim 68, wherein the micropellet cores have a diameter of less than 5 mm.

78. The pharmaceutical composition of claim 68, wherein the micropellet cores have a diameter of about 0.5 mm to about 2.0 mm.

79. The pharmaceutical composition of claim 68, wherein the enteric coating comprises hydroxypropyl cellulose, hydroxypropylmethyl acetate succinate, hydroxypropyl methyl cellulose acetate succinate, hydroxypropyl methylcellulose phthalate or methyl cellulose.

80. The pharmaceutical composition of claim 68, wherein the enteric coating comprises hydroxypropyl methyl cellulose acetate succinate or hydroxypropyl methylcellulose phthalate.

81. The pharmaceutical composition of claim 78, wherein the enteric coating comprises hydroxypropyl methyl cellulose acetate succinate or hydroxypropyl methylcellulose phthalate.

82. The pharmaceutical composition of claim 68, wherein the composition has a relative gastric acid resistance of 75% or more following incubation for 2 hours in 0.1 mol/l hydrochloric acid at pH 1.

83. The pharmaceutical composition of claim 80, wherein the composition has a relative gastric acid resistance of 75% or more following incubation for 2 hours in 0.1 mol/l hydrochloric acid at pH 1.

84. The pharmaceutical composition of claim 68, wherein the composition has a relative gastric acid resistance of 90% or more following incubation for 2 hours in a phosphate buffer at pH 5.

85. The pharmaceutical composition of claim 80, wherein the composition has a relative gastric acid resistance of 90% or more following incubation for 2 hours in a phosphate buffer at pH 5.

86. The pharmaceutical composition of claim 68, wherein the micropellet cores contain less than 3% water.

87. The pharmaceutical composition of claim 71, wherein the micropellet cores contain less than 3% water.

88. The pharmaceutical composition of claim 73, wherein the micropellet cores contain less than 3% water.

89. The pharmaceutical composition of claim 68, wherein the pancreatin micropellet cores consist essentially of 70% to 90% pancreatin by weight of the core; the at least one pharmaceutically acceptable binding agent is polyethylene glycol 4000; and the micropellet cores have a diameter of about 0.5 mm to about 2.0 mm.

90. The pharmaceutical composition of claim 68, wherein the dissolution of the enteric coated pancreatin micropellets is determined according to United States Pharmacopoeia monograph for pancrelipase delayed-release capsules.

91. A delayed-release oral pharmaceutical composition, the composition comprising:
 (a) pancreatin micropellet cores consisting of
  (i) pancreatin;
  (ii) at least one pharmaceutically acceptable binding agent;
  (iii) optionally, at least one pharmaceutically acceptable excipient, wherein synthetic oils are not pharmaceutically acceptable excipients; and
  (iv) an enzyme-friendly organic solvent, wherein synthetic oils are not enzyme-friendly organic solvents; and
 (b) an enteric coating on the cores, wherein the enteric coating is substantially free of monomeric phthalic acid esters;
 wherein the composition has a relative gastric acid resistance of 75% or more following incubation for 2 hours in a phosphate buffer solution at pH 5; and
 wherein at least 65% of lipase activity in the enteric coated pancreatin micropellets is released in 30 minutes in a phosphate buffer solution at pH 6.0 at 37° C., in a dissolution apparatus, using a paddle speed of 50 rpm, following 2 hours incubation in a gastric juice without enzymes at 37° C., in a dissolution apparatus, using a speed of 100 rpm.

92. The pharmaceutical composition of claim 91, wherein the optional pharmaceutically acceptable excipient is selected from the group consisting of fillers and glidants.

93. The pharmaceutical composition of claim 92, wherein the enteric coating comprises a plasticizer including cetyl alcohol and triethyl citrate.

94. The pharmaceutical composition of claim 91, wherein the enzyme-friendly organic solvent is selected from the group consisting of methanol, ethanol, 1-propanol, 2-propanol, 2-butanol, tert-butanol, and mixtures thereof.

95. A delayed-release oral pharmaceutical composition, the composition comprising:
 (a) pancreatin micropellet cores comprising pancreatin, at least one pharmaceutically acceptable binding agent, and an enzyme-friendly organic solvent, wherein synthetic oils are not pharmaceutically acceptable binding agents and wherein synthetic oils are not enzyme-friendly organic solvents; and
 (b) an enteric coating on the cores, wherein the enteric coating is substantially free of monomeric phthalic acid esters;
 wherein the enteric coated micropellets have a diameter from about 0.7 mm to about 1.6 mm;
 wherein, after storage for 5 months under slightly aggravated storage conditions, the composition has a relative gastric acid resistance of 75% or more following incubation for 2 hours in a phosphate buffer solution at pH 5, wherein slightly aggravated storage conditions comprise storing the enteric coated micropellets in hard gelatin capsules at 30° C. and 65% relative humidity.

96. The pharmaceutical composition of claim 95, wherein the enteric coating comprises a plasticizer including cetyl alcohol and triethyl citrate.

97. The pharmaceutical composition of claim 95, wherein the enzyme-friendly organic solvent is selected from the group consisting of methanol, ethanol, 1-propanol, 2-propanol, 2-butanol, tert-butanol, and mixtures thereof.

98. The pharmaceutical composition of claim 45, wherein the pancreatin micropellet cores comprise
 (i) 70% to 90% pancreatin by weight of the core,
 (ii) 10% to 30% of the at least one pharmaceutically acceptable binding agent by weight of the core, and
 (iii) up to 5% of the enzyme-friendly organic solvent by weight of the core.

99. The pharmaceutical composition of claim 98, wherein the at least one pharmaceutically acceptable binding agent is polyethylene glycol 4000.

100. The pharmaceutical composition of claim 91, wherein the pancreatin micropellet cores comprise
 (i) 70% to 90% pancreatin by weight of the core,
 (ii) 10% to 30% of the at least one pharmaceutically acceptable binding agent by weight of the core,
 (iii) from 0% to 5% of the optional at least one pharmaceutically acceptable excipient by weight of the core, and
 (iv) up to 5% of the enzyme-friendly organic solvent by weight of the core.

101. The pharmaceutical composition of claim 100, wherein the at least one pharmaceutically acceptable binding agent is polyethylene glycol 4000.

* * * * *